United States Patent
Arista et al.

(10) Patent No.: US 7,745,458 B2
(45) Date of Patent: Jun. 29, 2010

(54) AZABICYCLO (3, 1, 0) HEXAN DERIVATIVES USEFUL AS MODULATORS OF DOPAMINE D3 RECEPTORS

(75) Inventors: Luca Arista, Verona (IT); Anna Checchia, Verona (IT); Gabriella Gentile, Verona (IT); Dieter Hamprecht, Verona (IT); Fabrizio Micheli, Verona (IT)

(73) Assignee: Glaxo Group Limited, Greenford, Middlesex (GB)

( * ) Notice: Subject to any disclaimer, the term of this patent is extended or adjusted under 35 U.S.C. 154(b) by 4 days.

(21) Appl. No.: 12/064,123

(22) PCT Filed: Aug. 18, 2006

(86) PCT No.: PCT/EP2006/008201
§ 371 (c)(1),
(2), (4) Date: Aug. 13, 2008

(87) PCT Pub. No.: WO2007/022934
PCT Pub. Date: Mar. 1, 2007

(65) Prior Publication Data
US 2009/0221618 A1    Sep. 3, 2009

(30) Foreign Application Priority Data
Aug. 22, 2005  (GB) ................ 0517191.3

(51) Int. Cl.
*A01N 43/42*    (2006.01)
*A61K 31/44*    (2006.01)
*C07D 239/00*   (2006.01)
*C07D 239/02*   (2006.01)
*C07D 261/04*   (2006.01)
*C07D 261/14*   (2006.01)
*C07D 233/00*   (2006.01)
*C07D 233/14*   (2006.01)
*C07D 233/60*   (2006.01)

(52) U.S. Cl. ............... 514/292; 514/293; 544/242; 544/312; 548/245; 548/315.1; 548/331.1; 548/334.1

(58) Field of Classification Search ........... 514/292, 514/293; 544/242, 312; 548/245, 315.1, 548/331.1, 334.1
See application file for complete search history.

(56) References Cited

U.S. PATENT DOCUMENTS

2007/0142438 A1   6/2007   Arista et al. ........... 514/341

(Continued)

FOREIGN PATENT DOCUMENTS

| WO | WO02/40471    | 5/2002 |
| WO | WO03/035622   | 5/2003 |
| WO | WO2005/080382 | 9/2005 |

OTHER PUBLICATIONS

U.S. Appl. No. 11/917,352, filed Jul. 13, 2006, Arista et al.
(Continued)

*Primary Examiner* — Sreeni Padmanabhan
*Assistant Examiner* — Sarah Pihonak
(74) *Attorney, Agent, or Firm* — James M. Kanagy; Edward R. Gimmi; Charles M. Kinzig

(57) ABSTRACT

The present invention relates to novel compounds of formula (I) or a salt thereof:

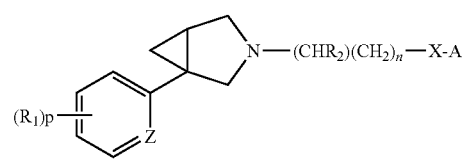

wherein:
p is 0, 1, 2, 3, 4 or 5;
$R_1$ is independently selected from a group consisting of: halogen, hydroxy, cyano, $C_{1-4}$alkyl, halo$C_{1-4}$alkyl, $C_{1-4}$alkoxy, halo$C_{1-4}$alkoxy, $C_{1-4}$alkanoyl and $SF_5$;
n is 3 or 4;
$R_2$ is hydrogen or $C_{1-4}$alkyl;
n is 2 or 3;
X is —$CH_2$—, —O— or —S—;
Z may be —CH— or N;
A is a group P or P1,
wherein P is

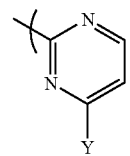

and P1 is

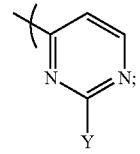

and
Y is hydrogen, —OH, $C_{1-4}$alkyl, halo$C_{1-4}$alkyl, phenyl or a heteroaromatic group, wherein the phenyl and the heteroaromatic group are optionally substituted by one or two substituents selected from a group consisting of $C_{1-4}$alkyl, halo$C_{1-4}$alkyl, $C_{1-4}$alkoxy and halo$C_{1-4}$alkoxy;
processes for their preparation, intermediates used in these processes, pharmaceutical compositions containing them and their use in therapy, as modulators of dopamine $D_3$ receptors, e.g. to treat substance related disorders, as antipsychotic agents premature ejaculation or cognition impairment.

11 Claims, No Drawings

U.S. PATENT DOCUMENTS

| | | | |
|---|---|---|---|
| 2007/0249642 A1 | 10/2007 | Bertani et al. | 514/269 |
| 2008/0058398 A1 | 3/2008 | Anderton et al. | 514/374 |
| 2008/0167357 A1 | 7/2008 | Hamprecht et al. | 514/384 |
| 2008/0176917 A1 | 7/2008 | Andreotti et al. | 514/384 |
| 2008/0227837 A1 | 9/2008 | Arista et al. | 514/384 |
| 2008/0242715 A1 | 10/2008 | Capelli et al. | 514/384 |
| 2009/0030062 A1 | 1/2009 | Gentile et al. | 514/412 |
| 2009/0036461 A1 | 2/2009 | Hamprecht et al. | 514/252.06 |
| 2009/0124629 A1 | 5/2009 | Bonanomi et al. | 514/252.06 |
| 2009/0221593 A1 | 9/2009 | Bonanomi et al. | 514/249 |

OTHER PUBLICATIONS

U.S. Appl. No. 12/295,024, filed Mar. 30, 2007, Bertani et al.
U.S. Appl. No. 12/295,304, filed Mar. 30, 2007, Bertani et al.

AZABICYCLO (3, 1, 0) HEXAN DERIVATIVES USEFUL AS MODULATORS OF DOPAMINE D3 RECEPTORS

The present invention relates to novel compounds, processes for their preparation, intermediates used in these processes, pharmaceutical compositions containing them and their use in therapy, as modulators of dopamine $D_3$ receptors.

WO 2002/40471 (SmithKline Beecham) discloses certain benzazepine compounds having activity at the dopamine $D_3$ receptor.

A new class of compounds which have affinity for dopamine receptors, in particular the dopamine $D_3$ receptor has been found. These compounds have potential in the treatment of conditions wherein modulation, especially antagonism/inhibition, of the $D_3$ receptor is beneficial, e.g. to treat drug dependency or as antipsychotic agents.

The present invention provides a compound of formula (I) or a salt thereof:

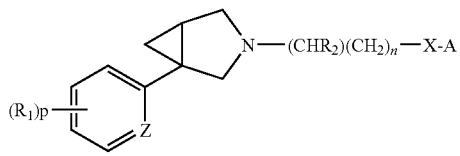

(I)

wherein:

p is 0, 1, 2, 3, 4 or 5;

$R_1$ is independently selected from a group consisting of: halogen, hydroxy, cyano, $C_{1-4}$alkyl, halo$C_{1-4}$alkyl, $C_{1-4}$alkoxy, halo$C_{1-4}$alkoxy, $C_{1-4}$alkanoyl and $SF_5$;

n is 3 or 4;

$R_2$ is hydrogen or $C_{1-4}$alkyl;

n is 2 or 3;

X is —$CH_2$—, —O— or —S—;

Z may be —CH— or N;

A is a group P or P1, wherein P is

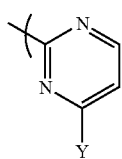

and P1 is

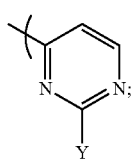

and

Y is hydrogen, —OH, $C_{1-4}$alkyl, halo$C_{1-4}$alkyl, phenyl or a heteroaromatic group, wherein the phenyl and the heteroaromatic group are optionally substituted by one or two substituents selected from a group consisting of $C_{1-4}$alkyl, halo$C_{1-4}$alkyl, $C_{1-4}$alkoxy and halo$C_{1-4}$alkoxy.

In a further embodiment, the present invention provides a compound of formula (IA) or a salt thereof:

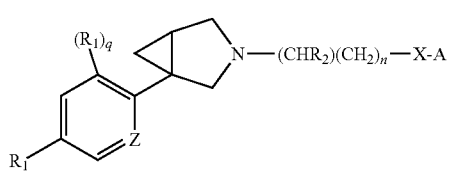

(IA)

wherein:

q is 0 or 1;

$R_1$ is independently selected from a group consisting of: halogen, hydroxy, cyano, $C_{1-4}$alkyl, halo$C_{1-4}$alkyl, $C_{1-4}$alkoxy, halo$C_{1-4}$alkoxy, $C_{1-4}$alkanoyl and $SF_5$;

n is 3 or 4;

$R_2$ is hydrogen or $C_{1-4}$alkyl;

n is 2 or 3;

X is —$CH_2$—, —O— or —S—;

Z may be —CH— or N;

A is a group P or P1, wherein P is

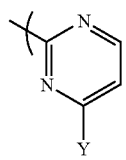

and P1 is

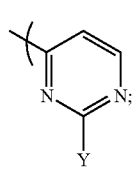

and

Y is hydrogen, —OH, $C_{1-4}$alkyl, halo$C_{1-4}$alkyl, phenyl or a heteroaromatic group, wherein the phenyl and the heteroaromatic group are optionally substituted by one or two substituents selected from a group consisting of $C_{1-4}$alkyl, halo$C_{1-4}$alkyl, $C_{1-4}$alkoxy and halo$C_{1-4}$alkoxy.

In one embodiment, the present invention provides a compound of formula (IB) or a salt thereof:

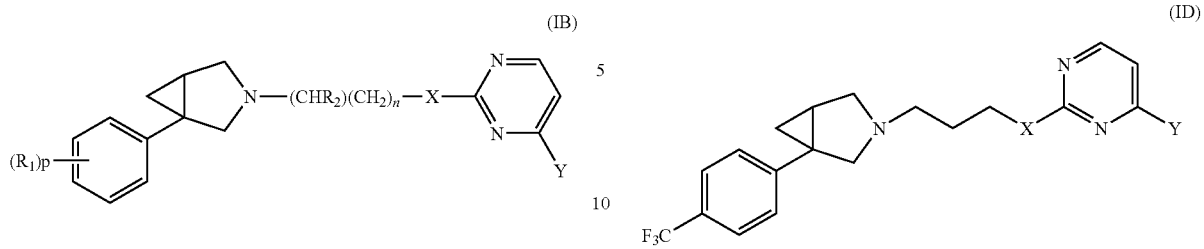

wherein:

p is 0, 1, 2, 3, 4 or 5;

$R_1$ is independently selected from a group consisting of: halogen, hydroxy, cyano, $C_{1-4}$alkyl, halo$C_{1-4}$alkyl, $C_{1-4}$alkoxy, halo$C_{1-4}$alkoxy, $C_{1-4}$alkanoyl and $SF_5$;

n is 3 or 4;

$R_2$ is hydrogen or $C_{1-4}$alkyl;

n is 2 or 3;

X is —$CH_2$— or —S—; and

Y is hydrogen, —OH, $C_{1-4}$alkyl, halo$C_{1-4}$alkyl, phenyl or a heteroaromatic group, wherein the phenyl and the heteroaromatic group are optionally substituted by one or two substituents selected from a group consisting of $C_{1-4}$alkyl, halo$C_{1-4}$alkyl, $C_{1-4}$alkoxy and halo$C_{1-4}$alkoxy.

In another embodiment, the present invention provides a compound of formula (IC) or a salt thereof:

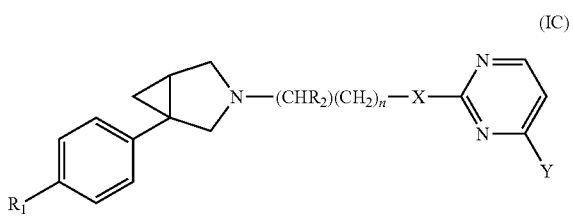

wherein:

$R_1$ is independently selected from a group consisting of: halogen, hydroxy, cyano, $C_{1-4}$alkyl, halo$C_{1-4}$alkyl, $C_{1-4}$alkoxy, halo$C_{1-4}$alkoxy, $C_{1-4}$alkanoyl and $SF_5$;

n is 3 or 4;

$R_2$ is hydrogen or $C_{1-4}$alkyl;

n is 2 or 3;

X is —$CH_2$— or —S—; and

Y is hydrogen, —OH, $C_{1-4}$alkyl, halo$C_{1-4}$alkyl, phenyl or a heteroaromatic group, wherein the phenyl and the heteroaromatic group are optionally substituted by one or two substituents selected from a group consisting of $C_{1-4}$alkyl, halo$C_{1-4}$alkyl, $C_{1-4}$alkoxy and halo$C_{1-4}$alkoxy.

In one embodiment, a compound of formula (ID) or a salt thereof is provided:

wherein X is —$CH_2$—, —O— or —S—, and Y is hydrogen, halo$C_{1-4}$alkyl or phenyl, wherein the phenyl is optionally substituted by $C_{1-4}$alkoxy, —OH or $C_{1-4}$alkyl.

The term "$C_{1-4}$alkyl" refers to an alkyl group having from one to four carbon atoms, in all isomeric forms, such as methyl, ethyl, propyl, isopropyl, butyl, isobutyl, sec-butyl and tert-butyl. The term "n-$C_{1-4}$alkyl" refers to the unbranched alkyls as defined above.

The term "$C_{1-4}$alkoxy" refers to a straight chain or branched chain alkoxy (or "alkyloxy") group having from one to four carbon atoms, such as methoxy, ethoxy, propoxy, isopropoxy, butoxy, isobutoxy, sec-butoxy and tert-butoxy.

The term "$C_{1-4}$alkanoyl" refers to an alkanoyl group having from one to four carbon atoms, such as methanoyl (or "formyl"), ethanoyl (or "acetyl"), propanoyl, isopropanoyl, butanoyl, isobutanoyl and sec-butanoyl.

The term "$SF_5$" refers to pentafluorosulfanyl.

The term "halogen" and its abbreviation "halo" refer to fluorine (F), chlorine (Cl), bromine (Br) or iodine (I). Where the term "halo" is used before another group, it indicates that the group is substituted by one, two or three halogen atoms. For example, "halo$C_{1-4}$alkyl" refers to groups such as trifluoromethyl, bromoethyl, trifluoropropyl, and other groups derived from $C_{1-4}$alkyl groups as defined above; and the term "halo$C_{1-4}$alkoxy" refers to groups such as trifluoromethoxy, bromoethoxy, trifluoropropoxy, and other groups derived from $C_{1-4}$alkoxy groups as defined above.

The term "heteroaromatic group" refers to a 5- or 6-membered aromatic group containing 1, 2, 3 or 4 heteroatoms, for example from 1 to 3 heteroatoms, selected from O, N and S. For example, when the group contains 2, 3 or 4 heteroatoms, one may be selected from O, N and S and the remaining heteroatoms may be N. Examples of 5-membered heteroaromatic groups include pyrrolyl, imidazolyl, pyrazolyl, oxazolyl, furazanyl, isoxazolyl, triazolyl, oxadiazolyl, isothiazolyl, thiazolyl, furyl, thienyl and thiadiazolyl. Examples of 6-membered heteroaromatic groups include pyridyl, triazinyl, pyridazinyl, pyrimidinyl and pyrazinyl.

Any of these groups may be attached to the rest of the molecule at any suitable position.

As used herein, the term "salt" refers to any salt of a compound according to the present invention prepared from an inorganic or organic acid or base, quaternary ammonium salts and internally formed salts. Physiologically acceptable salts are particularly suitable for medical applications because of their greater aqueous solubility relative to the parent compounds. Such salts must clearly have a physiologically acceptable anion or cation. Suitably physiologically acceptable salts of the compounds of the present invention include acid addition salts formed with inorganic acids such as hydrochloric, hydrobromic, hydroiodic, phosphoric, metaphosphoric, nitric and sulfuric acids, and with organic acids, such as tartaric, acetic, trifluoroacetic, citric, malic, lactic, fumaric, benzoic, formic, propionic, glycolic, gluconic, maleic, succinic, camphorsulfuric, isothionic, mucic, gentisic, isonicotinic, saccharic, glucuronic, furoic, glutamic, ascorbic, anthranilic, salicylic, phenylacetic, mandelic, embonic (pamoic), methanesulfonic, ethanesulfonic, pantothenic, stearic, sulfinilic, alginic, galacturonic and arylsulfonic, for example benzenesulfonic and p-toluenesulfonic, acids; base addition salts formed with alkali metals and alkaline earth metals and organic bases such as N,N-dibenzylethylenediamine, chloroprocaine, choline, diethanolamine, ethylenediamine, meglumaine (N-methylglucamine), lysine and procaine; and internally formed salts. Salts having a non-physiologically acceptable anion or cation are within the scope of the invention as useful intermediates for the preparation of physiologically acceptable salts and/or for use in non-therapeutic, for example, in vitro, situations.

In one embodiment, p is 1.

In another embodiment, p is 2.

In one embodiment, $R_1$ is haloC$_{1-4}$alkyl, for example $CF_3$.

In another embodiment, $R_1$ is haloC$_{1-4}$alkyl (such as CF3) or halogen (such as fluorine).

In one embodiment, $R_2$ is hydrogen.

In one embodiment, n is 3 and X is —CH$_2$—. In another embodiment, n is 3 and X is —S—.

In a still further embodiment, n is 3 and X is —O—.

In one embodiment, Y is hydrogen, haloC$_{1-4}$alkyl such as $CF_3$, or phenyl optionally substituted by haloC$_{1-4}$alkoxy such as methoxy.

In another embodiment, Y is —OH or C$_{1-4}$alkyl.

In one embodiment A is P.

In another embodiment A is P1.

In one embodiment Z is CH. In another embodiment Z is N.

In one embodiment q is 1. In another embodiment q is 0.

Certain groups/substituents included in the present invention may be present as isomers. The present invention includes within its scope all such isomers, including racemates, enantiomers, tautomers and mixtures thereof. Certain of the substituted heteroaromatic groups included in compounds of formula (I) may exist in one or more tautomeric forms. The present invention includes within its scope all such tautomeric forms, including mixtures.

It will be appreciated by the person skilled in the art that group P, as above defined in compounds of formula (I), may exist in the tautomeric forms (Pa) and (Pb) as below described when Y is —OH:

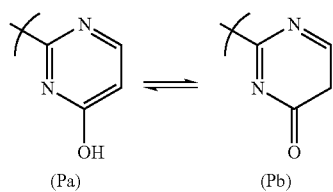

Both tautomeric forms are intended to be included within the scope of this invention.

It will be appreciated by the person skilled in the art that group P1, as above defined in compounds of formula (I), may exist in the tautomeric forms (P1a) and (P1b) as below described when Y is —OH:

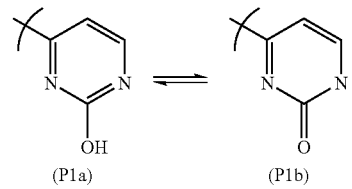

Both tautomeric forms are intended to be included within the scope of this invention.

It will be appreciated that compounds of formula (I) possess at least two chiral centres, namely at position 1 and 5 in the 3-azabicyclo[3.1.0]hexane portion of the molecule. ecause of the presence of the fused cyclopropane compounds of formula (I) are believed to have a "cis" disposition of the substituents (both groups linked to the bicyclic ring system are on the same face of this bicyclic ring system). Thus, the compounds may exist in two stereoisomers which are enantiomers with respect to the chiral centres in the cyclopropane. It will also be appreciated, in common with most biologically active molecules that the level of biological activity may vary between the individual stereoisomers of a given molecule. It is intended that the scope of the invention includes all individual stereoisomers (diastereoisomers and enantiomers) and all mixtures thereof, including but not limited to racemic mixtures, which demonstrate appropriate biological activity with reference to the procedures described herein.

In another embodiment of the present invention compounds of formula (I)' are provided which correspond to the compounds of formula (I) having "cis" disposition, represented by the bold highlight of the two bonds near the cyclopropyl moiety:

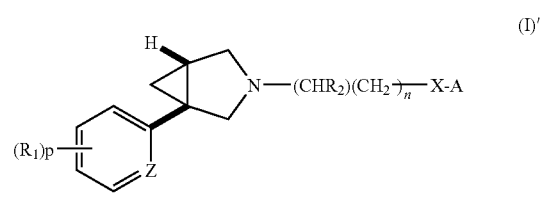

wherein p, $R_1$, $R_2$, n, X, A and Z are defined as above for compounds of formula (I).

In compounds of formula (I)' there are at least two chiral centres, which are located in the cyclopropane portion, as depicted below (the bold highlight of the bonds means the "cis" configuration):

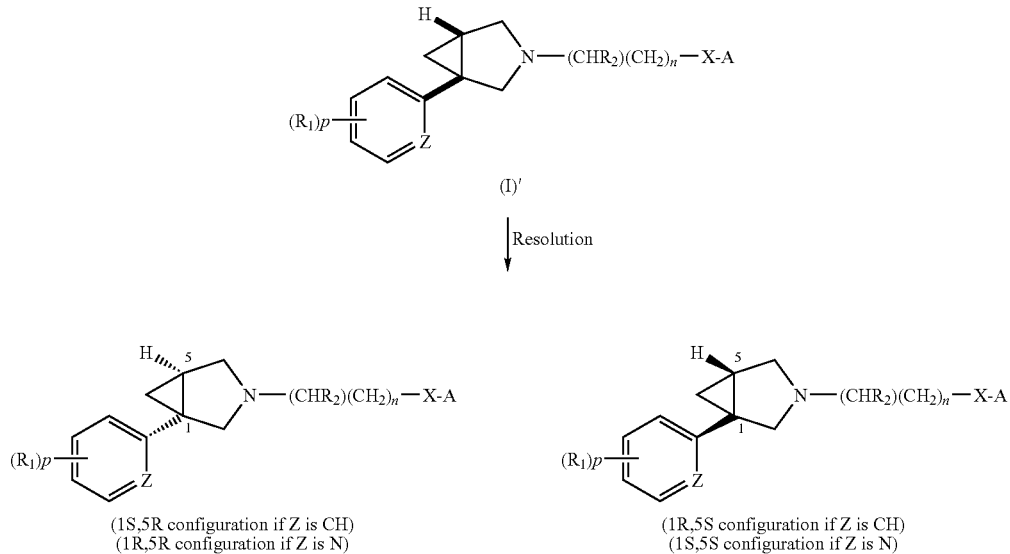

In a further embodiment of the present invention, there is provided a compound of formula (IL) or a salt thereof that correspond to a stereochemical isomer of a compound of formula (I), enriched in configuration (1S,5R) if z is CH or (1R,5R) if Z is N:

(IL)

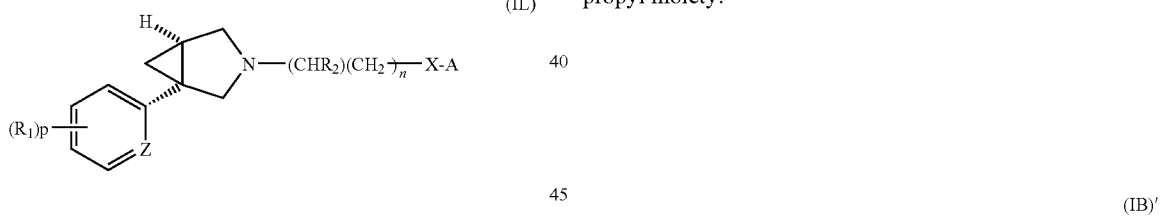

wherein p, $R_1$, $R_2$, n, X, A and Z are defined as above for compounds of formula (I).

In a further embodiment of the present invention, there is provided a compound of formula (IM) or a salt thereof that correspond to a stereochemical isomer of a compound of formula (IA) as above described, enriched in configuration (1S,5R) if z is CH or (1R, 5R) if Z is N:

(IM)

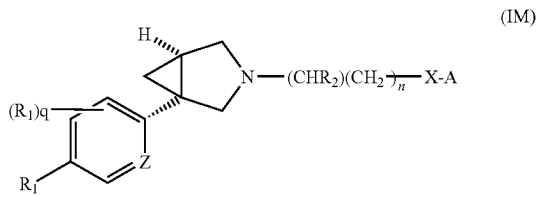

wherein q, $R_1$, $R_2$, n, X, A and Z are defined as above for compounds of formula (I).

In another embodiment of the present invention compounds of formula (IB)' are provided which correspond to the compounds of formula (IB) having "cis" disposition, represented by the bold highlight of the two bonds near the cyclopropyl moiety:

(IB)'

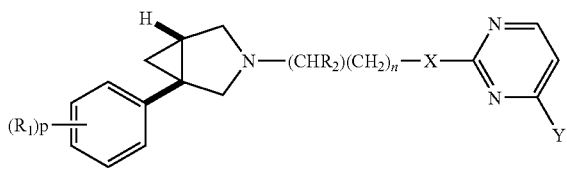

wherein p, $R_1$, $R_2$, n, X and Y are defined as above for compounds of formula (I).

In compounds of formula (IB)' there are at least two chiral centres, which are located in the cyclopropane portion, as depicted below (the bold highlight of the bonds means the "cis" configuration):

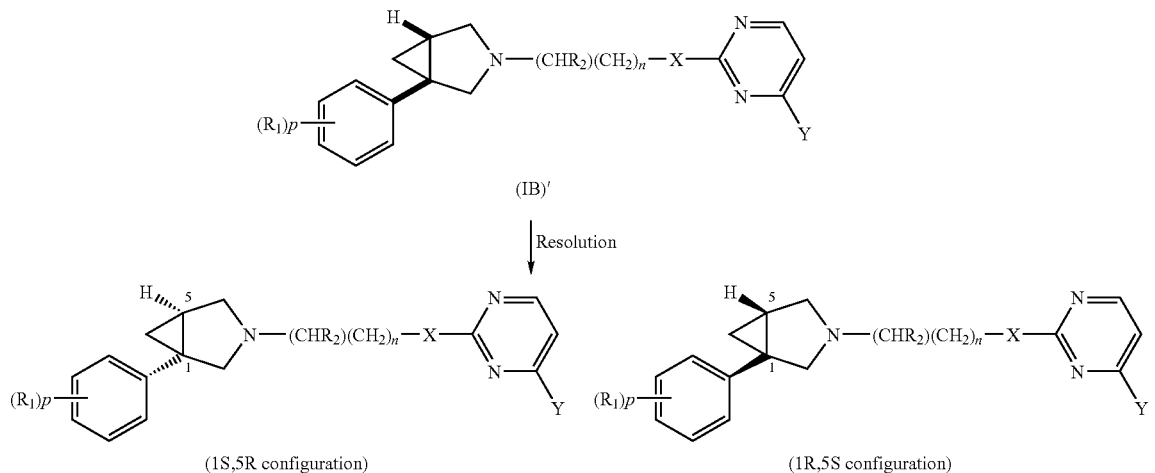

(IB)'

↓ Resolution (1S,5R configuration)    (1R,5S configuration)

In a further embodiment of the present invention, there is provided a compound of formula (IJ) or a salt thereof that correspond to a stereochemical isomer of a compound of formula (IB), enriched in configuration (1S,5R):

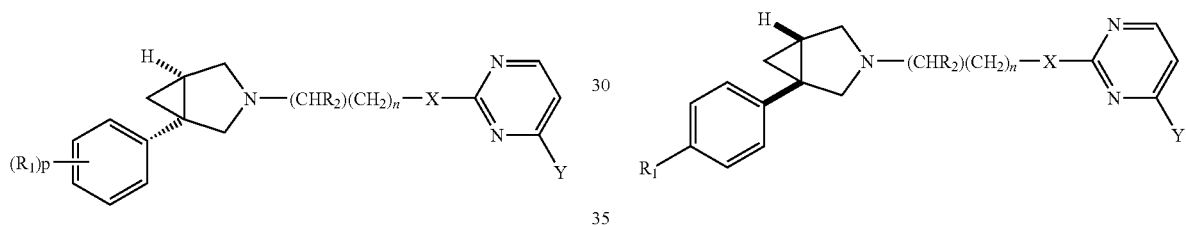

wherein p, $R_1$, $R_2$, n, X and Y are defined as above for compounds of formula (I).

In another embodiment of the present invention compounds of formula (IC)' are provided which correspond to the compounds of formula (IC) having "cis" disposition, represented by the bold highlight of the two bonds near the cyclopropyl moiety:

(IC)' wherein p, $R_1$, $R_2$, n, X and Y are defined as above for compounds of formula (I).

In compounds of formula (IC)' there are at least two chiral centres, which are located in the cyclopropane portion, as depicted below (the bold highlight of the bonds means the "cis" configuration):

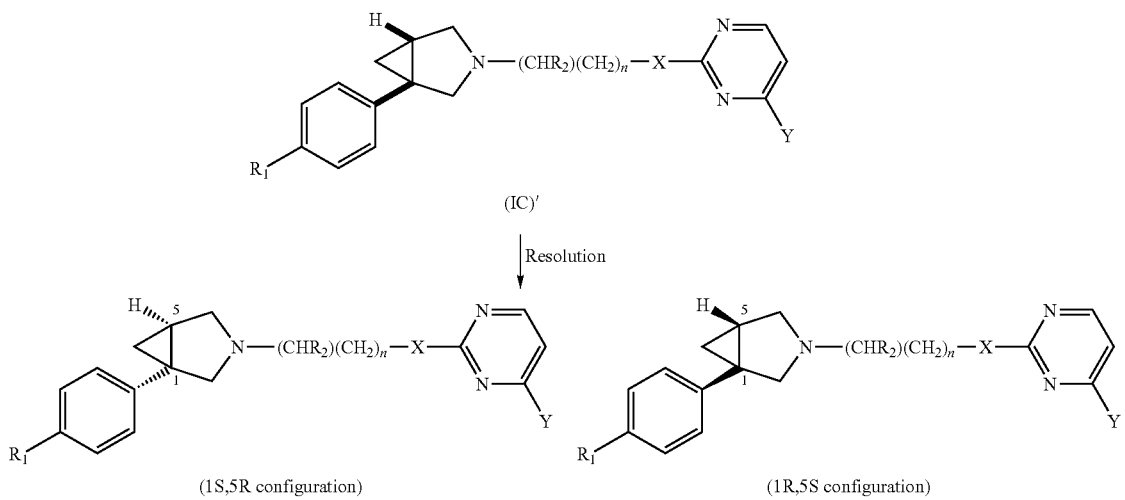

(IC)'

↓ Resolution (1S,5R configuration)    (1R,5S configuration)

In a further embodiment of the present invention, there is provided a compound of formula (IK) or a salt thereof that correspond to a stereochemical isomer of a compound of formula (IC), enriched in configuration (1S,5R):

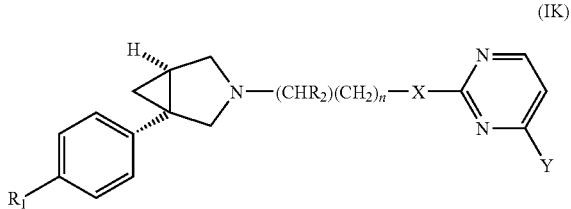

wherein p, $R_1$, $R_2$, n, X and Y are defined as above for compounds of formula (I).

In a further embodiment of the present invention, there is provided a compound of formula (IM) or a salt thereof that correspond to a stereochemical isomer of a compound of formula (IA) as above described, enriched in configuration (1S,5R) if z is CH or (1R, 5R) if Z is N:

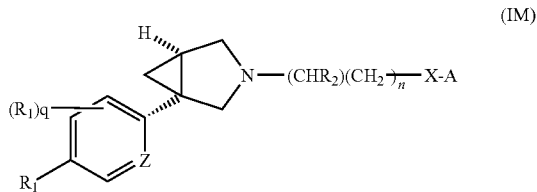

wherein q, $R_1$, $R_2$, n, X, A and Z are defined as above for compounds of formula (I).

In another embodiment, there is provided a compound of formula (IN) or a salt thereof,

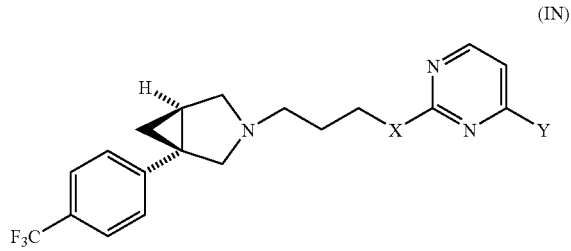

wherein X and Y are as defined for formula (ID) above.

It is intended in the context of the present invention that stereochemical isomers enriched in configuration (1S,5R) or (1R,5R) of formula (I) correspond in one embodiment to at least 90% enantiomeric excess. In another embodiment the isomers correspond to at least 95% enantiomeric excess. In another embodiment the isomers correspond to at least 99% enantiomeric excess.

The strategy for determining the absolute configuration of the compounds of the present invention comprised as a first step the preparation of the chiral intermediate, (1S,5R)-1-[4-(trifluoromethyl)phenyl]-3-azabicyclo[3.1.0]hexane:

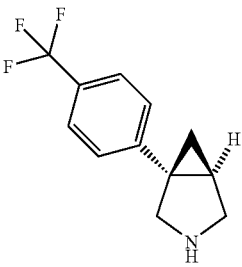

by using (S)-(+) acetyl mandelic acid as resolving agent.

In the literature the absolute configuration of a series of compounds similar to this chiral intermediate is known, see J. Med Chem 1981, 24(5), 481-90. For some compounds disclosed in the reference the absolute configuration was proved by single crystal X-ray analysis.

The assignment of the absolute configuration of the chiral intermediate, (1S,5R)-1-[4-(trifluoromethyl)phenyl]-3-azabicyclo[3.1.0]hexane, was confirmed by a single crystal X-ray structure obtained from a crystal of (1S,5R)-1-[4-(trifluoromethyl)phenyl]-3-azabicyclo[3.1.0]hexane, (S)-(+)-mandelic acid salt. Both the analysis based on the known configuration of the (S)-(+)-mandelic acid and on the basis of anomalous dispersion effects confirmed the assignment of this compound as being (1S,5R)-1-[4-(trifluoromethyl)phenyl]-3-azabicyclo[3.1.0]hexane. As this chiral intermediate was used for the preparation of all the example compounds of the present invention, the absolute configurations of all the example compounds disclosed herein were believed to be the same as the chiral intermediate, based on a reasonable assumption by a skilled person in the art.

Chiral molecules exhibit vibrational circular dichroism (VCD). Vibrational circular dichroism (VCD) is the differential interaction of a chiral molecule with left and right circularly polarized infrared radiation during vibrational excitation.

The VCD spectrum of a chiral molecule is dependent on its three-dimensional structure. Most importantly, the VCD spectrum of a chiral molecule is a sensitive function of its absolute configuration and, in the case of flexible molecules, of its conformation. In principle, therefore, VCD permits the determination of the structure of a chiral molecule. VCD spectra were first measured in the 1970s. Subsequently, VCD instrumentation has developed enormously in spectral range and in sensitivity. Currently, VCD spectra of liquids and solutions can be measured over the majority of the fundamental infrared (IR) spectral range ($v \geq 650$ cm-1) with high sensitivity at acceptable resolution (1-5 cm-1) using both dispersive and Fourier Transform (FT) VCD instrumentation. Very recently, commercial FT VCD instrumentation has become available, greatly enhancing the accessibility of VCD spectra.

The use of VCD as a reliable method for the determination of absolute configuration of chiral molecules is now well established (see for example Shah R D, et al., Curr Opin Drug Disc Dev 2001; 4:764-774; Freedman T B, et al., Helv Chim Acta 2002; 85:1160-1165; Dyatkin A B, et al. Chirality 2002; 14:215-219; Solladié-Cavallo A, Balaz M et al., Tetrahedron Assym 2001; 12:2605-2611; Nafie L A, et al. Circular dichroism, principles and applications, 2nd ed. New York: John Wiley & Sons; 2000. p 97-131; Nafie L A, et al. in: Yan B, Gremlish H-U, editors. Infrared and Raman spectroscopy of biological materials. New York: Marcel Dekker; 2001. p 15-54; Polavarapu P L, et al., J Anal Chem 2000; 366:727-

734; Stephens P J, et al., Chirality 2000; 12:172-179; Solladié-Cavallo A, et al., Eur J Org Chem 2002: 1788-1796).

The method entails comparison of observed IR and VCD spectra with calculations of the spectra for a specific configuration and provides information both on the absolute configuration and on the solution conformation.

Given an experimental spectrum of a chiral molecule whose absolute configuration and/or conformation are unknown and to be determined, the general procedure is as follows: 1) all possible structures are defined; 2) the spectra of these structures are predicted; and 3) predicted spectra are compared to the experimental spectrum. The correct structure will give a spectrum in agreement with experiment; incorrect structures will give spectra in disagreement with experiment.

VCD spectra are always measured simultaneously with vibrational unpolarized absorption spectra ("infrared (IR) spectra") and the two vibrational spectra together provide more information than does the VCD spectrum alone. In addition, vibrational unpolarized absorption spectra are automatically predicted simultaneously with VCD spectra.

For ab initio assignments, VCD and unpolarized IR spectra were calculated using the Gaussian 98 software package.

When chiral organic molecules are synthesized (or, if natural products, isolated) their optical rotations are routinely measured at one frequency or at a small number of discrete frequencies in the visible-near ultraviolet spectral region. Most commonly, the specific rotation at one frequency, that of the sodium D line, $[\alpha]_D$, is measured. The frequencies used lie below the threshold for electronic absorption, i.e., they are in the "transparent" spectral region. Optical rotation is a reflection of the enantiomeric excess (ee) of the sample and of the absolute configuration (AC) of the predominant enantiomer.

When the optical rotation at a given frequency for 100% ee is available, the measured optical rotation at the same frequency enables the sample ee to be determined. The determination of ee is the predominant application of discrete frequency, transparent spectral region optical rotations. In principle, the AC of the predominant enantiomer, if unknown, can also be determined. However, the determination of AC from optical rotation requires an algorithm which reliably predicts the optical rotations of molecules of known AC and a number of methodologies have been proposed for predicting discrete frequency, transparent spectral region optical rotations (Eliel E L, Wilen S H. Stereochemistry of organic compounds. New York: John Wiley & Sons; 1994. Chapter 13).

Very recently, developments in ab initio Density Functional Theory (DFT) have radically improved the accuracy of optical rotation calculation. As a result, for the first time it has become possible to routinely obtain ACs from optical rotations.

For ab initio OR assignments, the Dalton Quantum Chemistry Program was used.

Strategy above described for the determination of the absolute stereochemistry of the compounds of the invention may be considered reliable only for compounds in which Z is CH.

It will be appreciated that for use in medicine the salts of the compounds of the invention should be pharmaceutically (i.e physiologically) acceptable. Suitable pharmaceutically acceptable salts will be apparent to those skilled in the art and include for example acid addition salts formed with inorganic acids e.g. hydrochloric, hydrobromic, sulfuric, nitric or phosphoric acid; and organic acids e.g. succinic, maleic, acetic, fumaric, citric, tartaric, benzoic, p-toluenesulfonic, methanesulfonic or naphthalenesulfonic acid. Other non-pharmaceutically acceptable salts eg. oxalates, may be used, for example in the isolation of compounds of the invention and are included within the scope of this invention. Also included within the scope of the invention are solvates, hydrates, complexes and prodrugs of compounds of the invention. Pharmaceutical acceptable salts may also be prepared from other salts, including other salts, of the compound of formula (I) using conventional methods.

Certain of the compounds of the invention may form acid addition salts with less than one equivalent of the acid, or one or more equivalents of the acid. The present invention includes within its scope all possible stoichiometric and non-stoichiometric forms.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of the invention are within the scope of the invention. The compounds of formula (I) may readily be isolated in association with solvent molecules by crystallisation or evaporation of an appropriate solvent to give the corresponding solvates.

In addition, prodrugs are also included within the context of this invention. As used herein, the term "prodrug" means a compound which is converted within the body, e.g. by hydrolysis in the blood, into its active form that has medical effects. Pharmaceutically acceptable prudrugs are described in T. Higuchi and V. Stella, Prodrugs as Novel Delivery Systems, Vol. 14 of the A.C.S. Symposium Series, Edward B. Roche, ed., Bioreversible Carriers in Drug Design, American Pharmaceutical Association and Pergamon Press, 1987, and in D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference. Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol, sulfhydryl and amine functional groups of the compounds of structure (I). Further, in the case of a carboxylic acid (—COOH), esters may be employed, such as methyl esters, ethyl esters, and the like. Esters may be active in their own right and/or be hydrolysable under in vivo conditions in the human body. Suitable pharmaceutically acceptable in vivo hydrolysable ester groups include those which break down readily in the human body to leave the parent acid or its salt.

Furthermore, some of the crystalline forms of the compounds of structure (I) may exist as polymorphs, which are included in the present invention.

Those skilled in the art will appreciate that in the preparation of the compound of the invention or a solvate thereof it may be necessary and/or desirable to protect one or more sensitive groups in the molecule to prevent undesirable side reactions. Suitable protecting groups for use according to the present invention are well known to those skilled in the art and may be used in a conventional manner. See, for example, "Protective groups in organic synthesis" by T. W. Greene and P. G. M. Wuts (John Wiley & sons 1991) or "Protecting Groups" by P. J. Kocienski (Georg Thieme Verlag 1994).

Examples of suitable amino protecting groups include acyl type protecting groups (e.g. formyl, trifluoroacetyl, acetyl), aromatic urethane type protecting groups (e.g. benzyloxycarbonyl (Cbz) and substituted Cbz), aliphatic urethane protecting groups (e.g. 9-fluorenylmethoxycarbonyl (Fmoc), t-butyloxycarbonyl (Boc), isopropyloxycarbonyl, cyclohexyloxycarbonyl) and alkyl type protecting groups (e.g. benzyl, trityl, chlorotrityl). Examples of suitable oxygen protecting groups may include for example alky silyl groups, such as trimethylsilyl or tert-butyldimethylsilyl; alkyl ethers such as tetrahydropyranyl or tert-butyl; or esters such as acetate.

When a specific enantiomer of a compound of general formula (I) is required, this may be obtained for example by resolution of a corresponding enantiomeric mixture of a compound of formula (I) using conventional methods. Thus the required enantiomer may be obtained from the racemic compound of formula (I) by use of chiral HPLC procedure.

The present invention also includes isotopically-labelled compounds, which are identical to those recited in formula (I) and following, but for the fact that one or more atoms are replaced by an atom having an atomic mass or mass number different from the atomic mass or mass number usually found in nature. Examples of isotopes that can be incorporated into compounds of the invention and salts thereof include isotopes of hydrogen, carbon, nitrogen, oxygen, phosphorous, sulphur, fluorine, iodine, and chlorine, such as $^{2}H$, $^{3}H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$ and $^{125}I$. Compounds of the present invention and salts of said compounds that contain the aforementioned isotopes and/or other isotopes of other atoms are within the scope of the present invention. Isotopically-labelled compounds of the present invention, for example those into which radioactive isotopes such as $^{3}H$, $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of formula I and following of this invention can generally be prepared by carrying out the procedures disclosed in the Schemes and/or in the Examples below, by substituting a readily available isotopically labelled reagent for a non-isotopically labelled reagent.

In one embodiment of the present invention compounds are provided having a molecular weight of 800 or less. In another embodiment compounds are provided having a molecular weight of 600 or less. Generally, and without being limited thereto, such compounds may have higher oral bioavailability, and sometimes higher solubility and/or brain penetrancy. Molecular weight here refers to that of the unsolvated free base compound, excluding any molecular weight contributed by addition salts, solvent (e.g. water) molecules, prodrug molecular parts cleaved off in vivo, etc.

In general, the compounds or salts of the invention should be interpreted as excluding those compounds (if any) which are so chemically unstable, either per se or in water, that they are clearly unsuitable for pharmaceutical use through all administration routes, whether oral, parenteral or otherwise. Such compounds are known to the skilled chemist. Prodrugs or compounds which are stable ex vivo and which are convertable in the mammalian (e.g. human) body to the inventive compounds are however included.

Example compounds of the present invention include (1S,5R)-3-[4-(4-phenyl-2-pyrimidinyl)butyl]-1-[4-(trifluoromethyl)phenyl]-3-azabicyclo[3.1.0]hexane;

(1S,5R1)-[4-(trifluoromethyl)phenyl]-3-{4-[4-(trifluoromethyl)-2-pyrimidinyl]butyl}-3-azabicyclo[3.1.0]hexane;

(1S,5R)-3-[3-(2-pyrimidinylthio)propyl]-1-[4-(trifluoromethyl)phenyl]-3-azabicyclo[3.1.0]hexane;

(1S,5R)-3-[3-({4-[4-(methyloxy)phenyl]-2-pyrimidinyl}thio)propyl]-1-[4-(trifluoromethyl)phenyl]-3-azabicyclo[3.1.0]hexane;

2-[(3-{(1S,5R)-1-[4-(trifluoromethyl)phenyl]-3-azabicyclo[3.1.0]hex-3-yl}propyl)oxy]-4(1H)-pyrimidinone;

2-[(3-{(1S,5R)-1-[2-fluoro-4-(trifluoromethyl)phenyl]-3-azabicyclo[3.1.0]hex-3-yl}propyl)thio]-4(1H)-pyrimidinone;

4-[(3-{(1S,5R)-1-[4-(trifluoromethyl)phenyl]-3-azabicyclo[3.1.0]hex-3-yl}propyl)thio]-2(1H)-pyrimidinone;

(1S,5R)-3-{3-[(4-methyl-2-pyrimidinyl)thio]propyl}-1-[4-(trifluoromethyl)phenyl]-3-azabicyclo[3.1.0]hexane;

(1S,5R)-3-{3-[(4-methyl-2-pyrimidinyl)thio]propyl}-1-[4-(trifluoromethyl)phenyl]-3-azabicyclo[3.1.0]hexane;

2-(4-{(1S,5R)-1-[4-(trifluoromethyl)phenyl]-3-azabicyclo[3.1.0]hex-3-yl}butyl)-4-pyrimidinol 2-[(3-{(1R,5R)-1-[5-(trifluoromethyl)-2-pyridinyl]-3-azabicyclo[3.1.0]hex-3-yl}propyl)thio]-4-pyrimidinol;

2-[(3-{(1S,5R)-1-[4-(1-methylethyl)phenyl]-3-azabicyclo[3.1.0]hex-3-yl}propyl)thio]-4-pyrimidinol;

and salts thereof.

The present invention also provides a process for preparing a compound of formula (I) or a salt thereof as defined above, the process comprising:

(a) for compounds of formula (I) wherein X is —CH$_2$— and R$_2$ is hydrogen, reacting a compound of formula (II):

wherein n and A are as defined for formula (I), with a compound of formula (III):

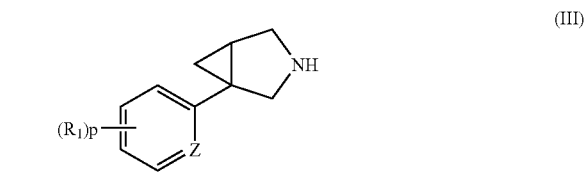

wherein p, Z and R$_1$ are as defined for formula (I); or (b) for a compound of formula (I), wherein X is —S—, reacting a compound of formula (IV):

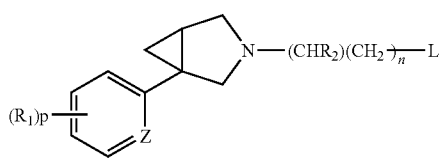

(IV)

wherein p, $R_1$, $R_2$, Z and n are as defined for formula (I) and L is a leaving group, with a compound of formula (V):

HS-A  (V)

wherein A is as defined for formula (I);

(b) for a compound of formula (I), wherein X is —O—, reacting a compound of formula (VI):

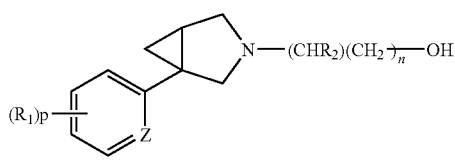

(VI)

wherein p, $R_1$, $R_2$, Z and n are as defined for formula (I), with a compound of formula (VII):

(VII)

wherein A is as defined for formula (I);

and thereafter optionally for process (a), (b) and for process (c):

(i) removing any protecting group(s); and/or (ii) forming a salt; and/or (iii) converting a compound of formula (I) or a salt thereof to another compound of formula (I) or a salt thereof.

Typical reaction conditions comprise:

For step (a) typical experimental conditions comprise reaction at room temperature in a dipolar solvent, such as THF, in the presence of an appropriate reducing agent, for example $NaBH(AcO)_3$ or $NaBH_4$, and of a catalytic amount of an acid, such as AcOH.

For step (b) typical experimental conditions comprise heating in an aprotic dipolar solvent (such as DMF or $CH_3CN$), in the presence of a catalyst, such as NaI, and of a suitable base, such as $K_2CO_3$.

For step (c) typical experimental conditions comprise reacting in an aprotic solvent (such as DMF) in the presence of an appropriate base such as NaH. Temperature may be kept low during formation of the anion, then it may be raised up to room temperature.

Compounds of formula (III) may be prepared by methods well known in the art (e.g. *J. Med. Chem.* 1981, 24, 481-490).

Interconversion of groups $R_1$ may be effected by methodology well known in the art (e.g. demethylation of a methoxy group resulting in a hydroxy group using a suitable Lewis acidic reagent such as boron tribromide in an inert solvent such as dichloromethane). sence of a suitable protecting group for the secondary amine, such as N-trifluoroacetyl.

In one aspect of the present invention, there is provided a synthetic process for the preparation of compounds of formula (III). This process comprises the following steps:

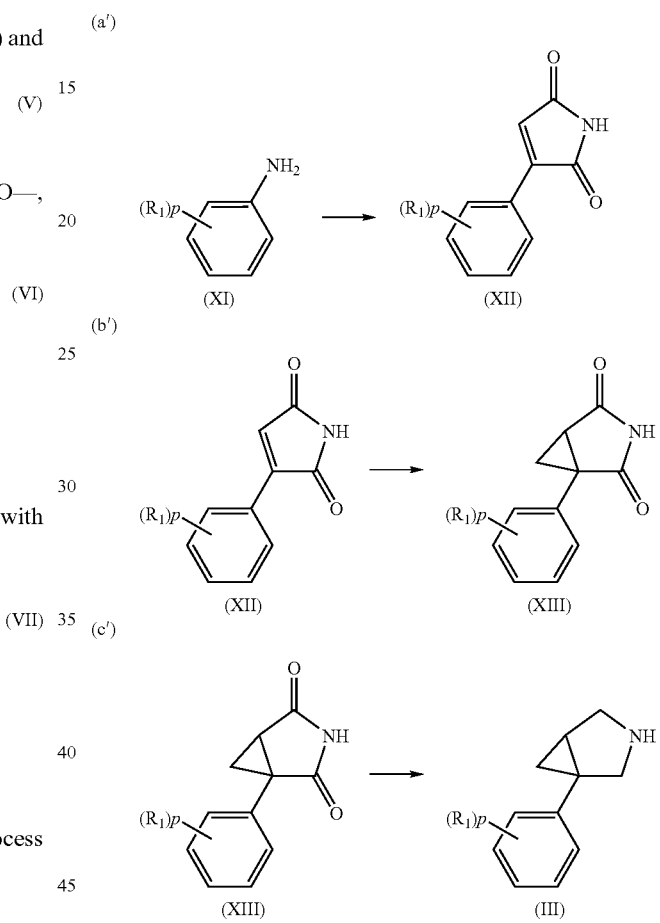

wherein:

step (a') means diazotation of an aniline (XI) followed by reaction with maleimide to give 3-arylmaleimide (XII);

step (b') means cycloropanation of (XII) to provide bicyclic imide (XIII);

step (c') means reduction of imide (XIII) to give compounds of formula (III).

Step (a') may be effected using conventional methods for the Meerwein reaction (e.g. *J. Am. Chem. Soc.* 1955, 77, 2313 describes the formation of arylmaleimides using this approach). Alternatively, in many cases this step is suitably performed applying a procedure where to a mixture of maleimide, an appropriate copper (II) salt such as anhydrous $CuCl_2$, and a suitable organonitrite, such as tert-butyl nitrite, in a compatible solvent, such as acetonitrile, is slowly added a solution of a compound of formula (XI). This is followed by allowing time to react as appropriate and a suitable workup.

Step (b') consists of slow addition of a solution of purified compound of formula (XII), or mixtures containing a compound of formula (XII), dissolved in a suitable solvent such as dimethylsulfoxide, to a solution of trimethylsulfoxonium iodide in a suitable solvent such as dimethylsulfoxide and a suitable base, such as sodium hydride. This is followed by allowing time to react as appropriate and a suitable workup.

Step (c') can be performed using a suitable reducing agent in a compatible solvent, such as borane in tetrahydrofuran or Red-Al® in toluene at an appropriate temperature, such as for example 65° C. in the case of borane as the reducing agent. This is followed by a suitable workup.

In another aspect of the present invention an alternative synthetic process for the preparation of compounds of formula (III) is provided, comprising the following steps:

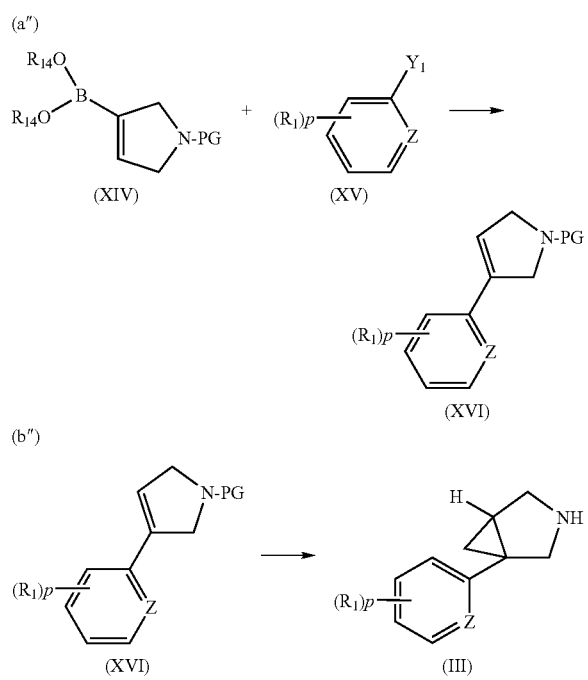

wherein:

$R_1$ and p are as defined for formula (I), $R_{14}O$ is a suitable alkoxy group, PG is an appropriate protecting group and $Y_1$ is halogen such as bromine, or a sulfonyloxy group such as trifluoromethylsulfonyloxy;

Wherein:

step (a″) means coupling reaction of a (2,5-dihydro-1H-pyrrol-3-yl)boronate (XIV) with the aromatic halogen or sulfonyloxy derivative (XV);

step (b″) means cyclopropanation of (XVI) followed by, if appropriate, deprotection to provide bicyclic amine (III).

Step (a″) may be effected using conventional methods for the Suzuki coupling, e.g. using tetrakis(triphenylphosphine) palladium(0) as the source of catalytic palladium(0) in the presence of cesium fluoride in an appropriate solvent such as tetrahydrofuran at a suitable temperature. $(R_{14}O)_2B$ may suitably be 4,4,5,5-tetramethyl-1,3,2-dioxaborolan-2-yl and PG benzyl, as reported in *Synlett* 2002, 5, 829-831.

Step (b″) consists of a cyclopropanation reaction effected for example using the reagent generated from trimethylsulfoxonium iodide and a suitable base such as sodium hydride, in a compatible solvent, for example dimethylsulfoxide. This is followed by a deprotection reaction.

Compounds of formula (II), wherein A is a group P and n' is 3, may be prepared trough the following synthetic reaction scheme:

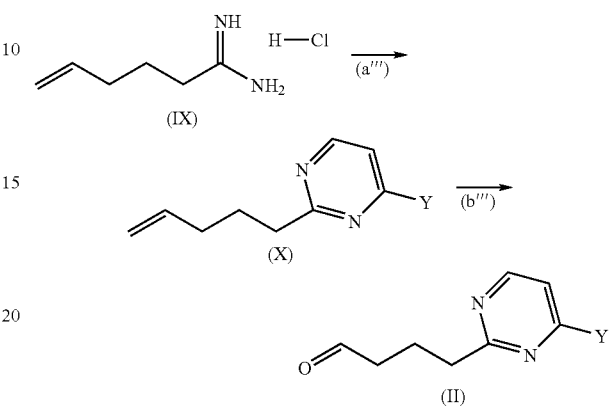

Step (a‴) may be effected reacting a compound of formula (IX) with the appropriate 1,4-α,β-unsaturated derivative or with the appropriate 1,3-dicarbonyl derivative in a dipolar solvent, such as $CH_3CN$ or EtOH, and with the optional presence of a base, such as $Na_2CO_3$.

Step (b‴) may be effected by stirring compounds of formula (X) in an appropriate solvent, such as a mixture THF/$H_2O$ (5:1), in the presence of a suitable oxidising system, such as $OsO_4$ in the presence of $NaIO_4$.

Compounds of formula (IX), may be obtained according to procedures well known in the art.

A compound of formula (IV) can be prepared by alkylation of a compound of formula (III) in the presence of a suitable base such as a tertiary amine, for example diisopropylethylamine, with a propyl derivative carrying two leaving groups of preferably differential reactivity in positions 1 and 3, for example 1-bromo-3-chloropropane.

A compound of formula (VI) can be prepared by alkylation of a compound of formula (III) in the presence of a suitable base such as a tertiary amine, for example triethylamine, with an appropriate derivative, carrying on one leaving group and an alcoholic function, for example 3-bromo-1-propanol, in a suitable solvent, such as THF. Typical reaction condition comprise heating at reflux, optionally in the presence of NaI.

A compound of formula (VII) may be obtained through oxidation of a compound of formula (VIII):

Typical reaction conditions comprise stirring compounds of formula (VII) in a suitable solvent, for example a mixture THF/MeOH (1:1), in the presence of an appropriate oxidising agent, for example a solution of Oxone® in water.

Interconversion reactions between compounds of formula (I) and salts thereof may be performed using methods well known in the art. Examples include:

(i) converting one or more of $R_1$ from alkoxy (e.g. methoxy) to hydroxy, (ii) converting one or more of $R_1$ from hydroxy to sulfonyloxy, such as alkylsulfonyloxy or haloalkylsulfonyloxy, e.g. methanesulfonyloxy or alkylsulfonyloxy or trifluoro-methanesulfonyloxy, (iii) converting one or more of $R_1$ from halogen or perfluoroalkylsulfonyloxy to cyano;

and optionally thereafter forming a salt of formula (I).

Compounds of formula (I) have been found to exhibit affinity for dopamine receptors, in particular the $D_3$ receptor, and are expected to be useful in the treatment of disease states which require modulation of such receptors, such as psychotic conditions. Such affinity is typically calculated from the $IC_{50}$ as the concentration of a compound necessary to displace 50% of the radiolabeled ligand from the receptor, and is reported as a "$K_i$" value calculated by the following equation:

$$K_i = \frac{IC_{50}}{1 + L/K_D}$$

where L=radioligand and $K_D$=affinity of radioligand for receptor (Cheng and Prusoff, *Biochem. Pharmacol.* 22:3099, 1973).

In the context of the present invention pKi (corresponding to the antilogarithm of Ki) is used instead of Ki and the compounds of the present invention typically show pKi greater than 7. In one aspect the present invention provides compounds of formula (I) having a pKi comprised between 7 and 8. In another aspect the present invention provides compounds of formula (I) having a pKi comprised between 8 and 9. In a further aspect the present invention provides compounds of formula (I) having a pKi greater than 9.

Many of the compounds of formula (I) have also been found to have greater affinity for dopamine $D_3$ than for $D_2$ receptors. The therapeutic effect of currently available antipsychotic agents (neuroleptics) is generally believed to be exerted via blockade of $D_2$ receptors; however this mechanism is also thought to be responsible for undesirable extrapyramidal side effects (eps) associated with many neuroleptic agents. It has been suggested that blockade of the recently characterised dopamine $D_3$ receptor may give rise to beneficial antipsychotic activity without significant eps. (see for example Sokoloff et al, Nature, 1990; 347: 146-151; and Schwartz et al, Clinical Neuropharmacology, Vol 16, No. 4, 295-314, 1993). In one embodiment compounds of the present invention are provided which have higher (e.g. $\geq 10\times$ or $\geq 100\times$ higher) affinity for dopamine $D_3$ than dopamine $D_2$ receptors (such affinity can be measured using standard methodology for example using cloned dopamine receptors—see herein). Said compounds may suitably be used as selective modulators of $D_3$ receptors.

From the localisation of $D_3$ receptors, it could also be envisaged that the compounds could also have utility for the treatment of a substance-related disorder where it has been suggested that $D_3$ receptors are involved (e.g. see Levant, 1997, Pharmacol. Rev., 49, 231-252). Examples of such a substance-related disorder include alcohol, cocaine, heroin and nicotine abuse. Compounds of formula (I) may be used for treatment of all aspects of drug dependency including drug intake, relapse to drug-seeking behaviour following abstinence and withdrawal symptoms from drugs of abuse such as alcohol, cocaine, opiates, nicotine, benzodiazepines and inhibition of tolerance induced by opioids. In addition, compounds of formula (I) and salts and solvates thereof may be used to reduce craving and therefore will be useful in the treatment of drug craving. Drug craving can be defined as the incentive motivation to self-administer a psychoactive substance that was previously consumed. Three main factors are involved in the development and maintenance of drug craving: (1) Dysphoric states during drug withdrawal can function as a negative reinforcer leading to craving; (2) Environmental stimuli associated with drug effects can become progressively more powerful (sensitization) in controlling drug seeking or craving, and (3) A cognition (memory) of the ability of drugs to promote pleasurable effects and to alleviate a dysphoric state during withdrawal. Craving may account for the difficulty that individuals have in giving up drugs of abuse and therefore contributes significantly to the development and maintenance of drug dependence.

The compounds of formula (I) are of potential use as antipsychotic agents for example in the treatment of schizophrenia, schizo-affective disorders, psychotic depression, mania, paranoid and delusional disorders. Furthermore, they could have utility as adjunct therapy in Parkinsons Disease, particularly with compounds such as L-DOPA and possibly dopaminergic agonists, to reduce the side effects experienced with these treatments on long term use (e.g. see Schwartz et al., Brain Res. Reviews, 1998, 26, 236-242). Other conditions which may be treated by the compounds include dyskinetic disorders such as Parkinson's disease, neuroleptic-induced parkinsonism and tardive dyskinesias; depression; anxiety, cognitive impairment including memory disorders such as Alzheimers disease, eating disorders, sexual dysfunction, sleep disorders, emesis, movement disorders, obsessive-compulsive disorders, amnesia, aggression, autism, vertigo, dementia, circadian rhythm disorders and gastric motility disorders e.g. IBS.

A wide range of psychiatric and neuropsychiatric disorders appear to be related to Obsessive-Compulsive Disorder, and form a family of related disorders referred to as obsessive-compulsive (OC) spectrum disorders. The compounds of formula (I) may be used for the treatment of an obsessive-compulsive spectrum disorder, including somatoform disorders such as body dysmorphic disorder and hyperchondriasis, bulimia nervosa, anorexia nervosa, binge eating, paraphilia and nonparaphilic sexual addictions, Sydeham's chorea, torticollis, autism, compulsive hoarding, and movement disorders, including Tourette's syndrome. As used herein, the phrase "obsessive-compulsive spectrum disorder" is intended to include Obsessive-Compulsive Disorder.

The compounds of formula (I) are also useful for the treatment of premature ejaculation.

Within the context of the present invention, the terms describing the indications used herein are classified in the Diagnostic and Statistical Manual of Mental Disorders, 4th Edition, published by the American Psychiatric Association (DSM-IV) and/or the International Classification of Diseases, 10th Edition (ICD-10). The various subtypes of the disorders mentioned herein are contemplated as part of the present invention. Numbers in brackets after the listed diseases below refer to the classification code in DSM-IV.

Within the context of the present invention, the term "substance-related disorder" includes:—

Substance-related disorders including Substance Use Disorders such as Substance Dependence, Substance Craving and A substance-related disorder; Substance-Induced Disorders such as Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-induced Persisting Amnestic Disorder, Alcohol-Induced Psychotic Disorder, Alcohol-induced Mood Disorder, Alcohol-Induced Anxiety Disorder, Alcohol-induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9); Caffeine Related Disorders such as Caffeine Intoxication (305.90), Caffeine-induced Anxiety Disorder, Caffeine-Induced Sleep Disorder and Caffeine-Related Disorder Not Otherwise Specified (292.9); Cannabis-Related Disorders such as Cannabis Dependence (304.30), Cannabis Abuse (305.20), Cannabis Intoxication (292.89), Cannabis Intoxication Delirium, Cannabis-induced Psychotic Disorder, Cannabis-Induced Anxiety Disorder and Cannabis-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-induced Psychotic Disorder, Cocaine-induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-induced Psychotic Disorder, Hallucinogen-Induced Mood Disorder, Hallucinogen-Induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide.

Within the context of the present invention, the term "psychotic disorder" includes:—

Schizophrenia including the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9).

In a further aspect therefore the present invention provides a method of treating a condition for which modulation [especially inhibition/antagonism (which may also translate into inverse agonism in constitutively active receptor systems)] of dopamine receptors (especially dopamine $D_3$ receptors) is beneficial, which comprises administering to a mammal (e.g. human) in need thereof an effective amount of a compound of formula (I) or a pharmaceutically (i.e physiologically) acceptable salt thereof. In one embodiment, the condition is a substance-related disorder, a psychotic disorder, an obsessive compulsive spectrum disorder or premature ejaculation.

The invention also provides the use of a compound of formula (I) or a salt thereof in the manufacture of a medicament for the treatment of a condition in a mammal for which modulation [especially inhibition/antagonism (which may also translate into inverse agonism in constitutively active receptor systems)] of dopamine receptors (especially dopamine $D_3$ receptors) is beneficial.

The invention also provides a compound of formula (I) or a salt thereof for use in the treatment of a condition in a mammal for which modulation [especially inhibition/antagonism (which may also translate into inverse agonism in constitutively active receptor systems)] of dopamine receptors (especially dopamine $D_3$ receptors) is beneficial.

In one embodiment, the compounds of the present invention are used in the treatment of a substance-related disorder, a psychotic disorder, an obsessive compulsive spectrum disorder or premature ejaculation.

Thus, a still further aspect the invention provides a method of treating a psychotic disorder (e.g. schizophrenia), a substance-related disorder or an obsessive compulsive spectrum disorder, which comprises administering to a mammal (e.g. human) in need thereof an effective amount of a compound of formula (I) as herein defined or a salt thereof.

Also provided is the use of a compound of formula (I) or a salt thereof in the manufacture of a medicament for the treatment of a psychotic disorder (e.g. schizophrenia), a substance-related disorder, an obsessive compulsive spectrum disorder or premature ejaculation.

Also provided is a compound of formula (I) or a salt thereof for use in the treatment of a psychotic disorder (e.g. schizophrenia), a substance-related disorder, an obsessive compulsive spectrum disorder or premature ejaculation.

Also provided is a compound of formula (I) or a salt thereof for use as a therapeutic substance in a mammal, e.g. for use in the treatment of any of the conditions described herein.

"Treatment" includes prophylaxis, where this is appropriate for the relevant condition(s).

For use in medicine, the compounds of the present invention are usually administered as a standard pharmaceutical composition. The present invention therefore provides in a further aspect a pharmaceutical composition comprising a compound of formula (I) or a pharmaceutically (i.e physiologically) acceptable salt thereof and a pharmaceutically (i.e physiologically) acceptable carrier. The pharmaceutical composition can be for use in the treatment of any of the conditions described herein.

The compounds of formula (I) may be administered by any convenient method, for example by oral, parenteral (e.g. intravenous), buccal, sublingual, nasal, rectal or transdermal administration and the pharmaceutical compositions adapted accordingly.

The compounds of formula (I) and their salts which are active when given orally can be formulated as liquids or solids, for example syrups, suspensions or emulsions, tablets, capsules and lozenges.

A liquid formulation will generally consist of a suspension or solution of the compound or salt in a suitable liquid carrier(s) for example an aqueous solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a pharmaceutically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluoro-chlorohydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

In one embodiment, the composition is in unit dose form such as a tablet, capsule or ampoule.

Each dosage unit for oral administration contains for example from 1 to 250 mg (and for parenteral administration contains for example from 0.1 to 25 mg) of a compound of the formula (I) or a salt thereof calculated as the free base.

The pharmaceutically acceptable compounds of the invention will normally be administered in a daily dosage regimen (for an adult patient) of, for example, an oral dose of between 1 mg and 500 mg, for example between 10 mg and 400 mg, e.g. between 10 and 250 mg or an intravenous, subcutaneous, or intramuscular dose of between 0.1 mg and 100 mg, for example between 0.1 mg and 50 mg, e.g. between 1 and 25 mg of the compound of the formula (I) or a salt thereof calculated as the free base, the compound being administered 1 to 4 times per day. Suitably the compounds will be administered for a period of continuous therapy, for example for a week or more.

Biological Test Methods

Functional potency and intrinsic activity of compounds of this invention can be measured by the following GTPγS scintillation proximity assay (GTPγS-SPA). Cells used in the study are Chinese Hamster Ovary (CHO) Cells.

Cell Line

CHO_D2

CHO_D3

Compounds may be tested according to two alternative protocols:

a) Cell membranes are prepared as follows. Cell pellets are resuspended in 10 volumes of 50 mM HEPES, 1 mM EDTA pH 7.4, using KOH. On the day the following proteases are added to the buffer just prior to giving the homogenisation buffer.

$2.12 \times 10^{-6}$M Leupeptin (Sigma L2884)—5000× stock=5 mg/ml in buffer 25 ug/ml Bacitracin (Sigma B0125)—1000× stock=25 mg/ml in buffer 1 mM PMSF—100× stock=17 mg/ml in 100% ethanol $2 \times 10^{-6}$M Pepstatin A—1000× stock=2 mM in 100% DMSO The cells are homogenised by 2×15 second bursts in a 1 liter Glass Waring blender in a class two biohazard cabinet. The resulting suspension is spun at 500 g for 20 mins (Beckman T21 centrifuge: 1550 rpm). The supernatant is withdrawn with a 25 ml pipette, aliquotted into pre-chilled centrifuge tubes and spun at 48,000 g to pellet membrane fragments (Beckman T1270: 23,000 rpm for 30 mins). The final 48,000 g pellet is resuspended in Homogenisation Buffer, (4× the volume of the original cell pellet). The 48,000 g pellet is resuspended by vortexing for 5 seconds and homogenized in a dounce homogenizer 10-15 stokes. The prep is distributed into appropriate sized aliquots, (200-1000 ul), in polypropylene tubes and store at −80° C. Protein content in the membrane preparations is evaluated with the Bradford protein assay.

The final top concentration of test drug is 3 uM in the assay and 11 points serial dilution curves 1:4 in 100% DMSO are carried out using a Biomek FX. The test drug at 1% total assay volume (TAV) is added to a solid, white, 384 well assay plate. 50% TAV of precoupled (for 90 mins at 4° C.) membranes, 5 µg/well, and Wheatgerm Agglutinin Polystyrene Scintillation Proximity Assay beads (RPNQ0260, Amersham), 0.25 mg/well, in 20 mM HEPES pH 7.4, 100 mM NaCl, 10 mM $MgCl_2$, 60 µg/ml saponin and 30 µM GDP is added. The third addition was a 20% TAV addition of either buffer, (agonist format) or $EC_{80}$ final assay concentration of agonist, Quinelorane, prepared in assay buffer (antagonist format). The assay was started by the addition of 29% TAV of GTPγ[$^{35}$S] 0.38 nM final (37 MBq/ml, 1160 Ci/mmol, Amersham). After all additions assay plates are spun down for 1 min at 1,000 rpm. Assay plates are counted on a Viewlux, 613/55 filter, for 5 min., between 2-6 hours after the final addition.

The effect of the test drug over the basal generates $EC_{50}$ value by an iterative least squares curve fitting programme, expressed in the table as $pEC_{50}$ (i.e. −log $EC_{50}$). The ratio between the maximal effect of the test drug and the maximal effect of full agonist, Quinelorane, generates the Intrinsic Activity (IA) value (i.e. IA=1 full agonist, IA<1 partial agonist). fpKi values of test drug are calculated from the $IC_{50}$ generated by "antagonist format" experiment, using Cheng & Prusoff equation: $fKi=IC_{50}/1+([A]/EC_{50})$ where: [A] is the concentration of the agonist 5-HT in the assay and $EC_{50}$ is the 5-HT $EC_{50}$ value obtained in the same experiment. fpKi is defined as −log fKi.

b) Cell membranes are prepared as follows. Cell pellets are resuspended in 10 volumes of 50 mM HEPES, 1 mM EDTA pH 7.4, using KOH. On the day the following proteases are added to the buffer just prior to giving the homogenisation buffer.

$10^{-4}$M Leupeptin (Sigma L2884)

25 ug/ml Bacitracin (Sigma B0125)

1 mM PMSF—100× stock=17 mg/ml in 100% ethanol $2×10^{-6}$M Pepstatin A—500× stock=1 mM in 100% ethanol The cells were homogenised within a glass waring blender for 2×15 secs in 200 mls of 50 mM HEPES+10-4M leupeptin+25 ug/ml bacitracin+1 mM EDTA+1 mM PMSF+2 uM Pepstatin A, (the latter 2 reagents added as fresh ×100 and ×500 stocks respectively in ethanol). The blender was plunged into ice for 5 mins after the first burst and 10-40 mins after the final burst to allow foam to dissipate. The material was then spun at 500 g for 20 mins and the supernatant spun for 36 mins at 48,000 g. The pellet was resuspended in the same buffer as above but without PMSF and Pepstatin A. The material was then forced through a 0.6 mm needle, made up to the required volume, (usually ×4 the volume of the original cell pellet), aliquoted and stored frozen at −80 deg C.

The final top concentration of test drug is 3 uM in the assay and 11 points serial dilution curves 1:4 in 100% DMSO are carried out using a Biomek FX. The test drug at 1% total assay volume (TAV) is added to a solid, white, 384 well assay plate. 50% TAV of precoupled (for 60 mins at RT) membranes, 5 µg/well, and Wheatgerm Agglutinin Polystyrene Scintillation Proximity Assay beads (RPNQ0260, Amersham), 0.25 mg/well, in 20 mM HEPES pH 7.4, 100 mM NaCl, 10 mM MgCl2, 60 µg/ml saponin and 30 µM GDP is added. The third addition was a 20% TAV addition of either buffer, (agonist format) or EC80 final assay concentration of agonist, Quinelorane, prepared in assay buffer (antagonist format). The assay was started by the addition of 29% TAV of GTP [35S] 0.38 nM final (37 MBq/ml, 1160 Ci/mmol, Amersham). After all additions assay plates are spun down for 1 min at 1,000 rpm. Assay plates are counted on a Viewlux, 613/55 filter, for 5 min., between 3-6 hours after the final addition.

The effect of the test drug over the basal generates EC50 value by an iterative least squares curve fitting programme, expressed in the table as pEC50 (i.e. −log EC50). The ratio between the maximal effect of the test drug and the maximal effect of full agonist, Quinelorane, generates the Intrinsic Activity (IA) value (i.e. IA=1 full agonist, IA<1 partial agonist). fpKi values of test drug are calculated from the $IC_{50}$ generated by "antagonist format" experiment, using Cheng & Prusoff equation: fKi=IC50/1+([A]/EC50) where: [A] is the concentration of the agonist Quinelorane in the assay and EC50 is the Quinelorane EC50 value obtained in the same experiment. fpKi is defined as −log fKi.

The compounds of the invention listed above have pKi values within the range of 7.0-10.5 at the dopamine D3 receptor In another embodiment, the compounds of the invention herein disclosed have pKi values within the range of 8.0-10.5 at the dopamine D3 receptor. pKi results are only estimated to be accurate to about ±0.3-0.5.

The compounds of the invention exemplified herein above have selectivity over D2 greater than 10. In another embodiment, the compounds of the invention exemplified herein above have selectivity over D2 greater than 20. In a further embodiment, the compounds of the invention exemplified herein above have selectivity over D2 greater than 30.

EXAMPLES

The invention is further illustrated by the following non-limiting examples.

Absolute stereochemistry of final compounds has been assigned on the basis of the reasonable assumption that absolute configurations of stereochemical centers in enatiopure compounds is maintained through the whole synthetic sequence.

All temperatures refer to ° C. Infrared spectra were measured on a FT-IR instrument. Compounds were analysed by direct infusion of the sample dissolved in acetonitrile into a mass spectra operated in positive electro spray (ES+) ionisation mode. Proton Magnetic Resonance ($^1$H-NMR) spectra were recorded at 400 MHz, chemical shifts are reported in ppm downfield (d) from $Me_4Si$, used as internal standard, and are assigned as singlets (s), broad singlets (bs), doublets (d), doublets of doublets (dd), triplets (t), quartets (q) or multiplets (m).

Experimental vibrational circular dichroism (VCD) spectra were measured using a Chirall® VCD spectrometer operating in the 2000-800 cm-1 frequency range. Spectra were measured at room temperature (23° C.) using a sealed transmission cell with barium fluoride windows and a path length of 100 microns. (Scan times varied from 60 to 120 minutes per isomer.) Sample solutions were typically prepared by dissolving 10 milligrams of each enantiomer in 100 microliters of deutero-chloroform ($CDCl_3$). For ab initio assignments, VCD and unpolarized IR spectra were calculated using the Gaussian 98 software package.1.

Optical rotations were measured using a (Perkin Elmer Model 241) polarimeter operating at 589 nm (Sodium source). Measurements were made using a 1 decimeter microcell thermostated at 23° C. Concentrations were typically 10 mg/ml (c=0.01). For ab initio OR assignments, the Dalton Quantum Chemistry Program was used.

Column chromathography was carried out over silica gel (Merck AG Darmstaadt, Germany). The following abbreviations are used in the text: EtOAc=ethyl acetate, Et$_2$O=dietyl ether, DMF=N,N'-dimethylformamide, MeOH=methanol, THF=tetrahydrofuran, AcOH=acetic acid; DCM=dichloromethane; SPE=solid phase extraction, SCX=strong cation exchanger, Tlc refers to thin layer chromatography on silica plates, and dried refers to a solution dried over anhydrous sodium sulphate, r.t. (RT) refers to room temperature, Rt=retention time, DMSO=dimethyl sulfoxide.

Absolute stereochemistry of final compounds has been assigned on the basis of the reasonable assumption that absolute configurations of stereochemical centers in enatiopure compounds is maintained through the whole synthetic sequence.

Preparation 1: (1S,5R)-1-[4-(trifluoromethyl)phenyl]-3-azabicyclo[3.1.0]hexane (P1)

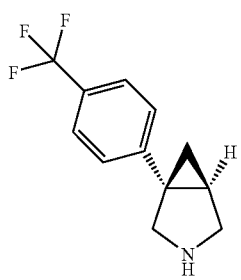

The title compound was prepared as reported in WO2005080382.

Preparation 2: (1S,5R)-3-(3-chloropropyl)-1-[4-(trifluoromethyl)phenyl]-3-azabicyclo[3.1.0]hexane (P2)

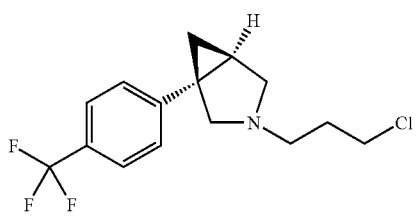

To a solution of (1S,5R)-1-[4-(trifluoromethyl)phenyl]-3-azabicyclo[3.1.0]hexane (P1, 1.00 g) in dry THF (5 mL), diisopropylethylamine (2.4 mL) and 1-bromo-3-chloropropane (3.7 mL) were added and the resulting mixture was heated at reflux for 3 hours. After cooling at room temperature it was diluted with ethyl acetate (30 mL) washed twice with a saturated solution of NH$_4$Cl in water (20 mL) and once with a saturated solution of NaHCO$_3$ in water (20 mL), dried over anhydrous Na$_2$SO$_4$ and concentrated under reduced pressure. The crude product was purified by silica gel chromatography eluting with cyclohexane/EtOAc 7:3 to give the title compound as a colourless oil (1.26 g).

NMR ($^1$H, CDCl$_3$): δ 7.50 (d, 2H) 7.19 (d, 2H), 3.59 (t, 2H), 3.33 (d, 1H), 3.09 (d, 1H), 2.58 (m, 2H), 2.66 (dd, 1H), 2.46 (dd, 1H), 1.92 (m, 2H), 1.74 (m, 1H), 1.67 (t, 1H), 0.81 (dd, 1H). MS (m/z): 304 [MH]$^+$.

Preparation 3: methyl 5-hexenimidoate hydrochloride (P3)

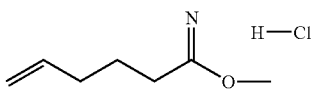

Through a stirred solution of 5-hexenenitrile (4 g) and MeOH (1.9 mL) in Et$_2$O (40 mL), at 0° C., HCl gas was bubbled for 10 minutes. Solvent was evaporated in vacuo and the residue triturated with Et$_2$O to give 3.7 g of the title compound as white solid, which was used in the subsequent step without further purification.

NMR ($^1$H, CDCl$_3$): δ 5.75 (m, 1H), 5.05 (m, 2H), 4.25 (s, 3H), 2.75 (t, 2H), 2.1 (dd, 2H), 1.85 (m, 2H). MS (m/z): 128 [MH]$^+$.

Preparation 4: 5-hexenimidamide hydrochloride (P4)

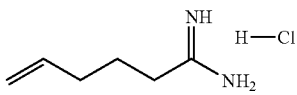

Methyl 5-hexenimidoate hydrochloride (P3, 1.5 g) was dissolved in NH$_3$ (2M in MeOH, 46 mL) and the mixture was heated to reflux for 2 h. Volatiles were evaporated in vacuo to give 1.45 g of the title compound as brown solid, which was used in the subsequent step without further purification.

NMR ($^1$H, DMSO-D6): δ 9.05 (s, 2H), 8.73 (s, 2H), 5.80 (m, 1H), 5.04 (m, 2H), 2.39 (m, 2H), 2.05 (m, 2H), 1.70 (m, 2H). MS (m/z): 113 [MH]$^+$.

Preparation 5: 2-(4-penten-1-yl)-4-phenylpyrimidine (P5)

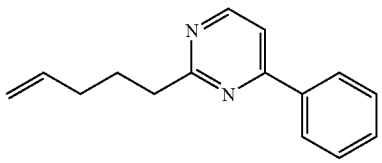

A mixture of 5-hexenimidamide hydrochloride (P4, 500 mg), 3-phenyl-2-propynal (398 mg), and sodium carbonate (786 mg) in acetonitrile (15 mL) was irradiated in a microwave synthesizer at 120° C. for 40 min and then allowed to cool. The solution was filtered and evaporated in vacuo. The residue was dissolved in dichloromethane and the organic layer was washed with H$_2$O, dried over Na$_2$SO$_4$, filtered and evaporated in vacuo. The crude was purified by column chromatography (eluting with ciclohexane/ethyl acetate 9/1) to give 142 mg of the title compound.

NMR (¹H, CDCl₃): δ 8.70 (d, 2H), 8.11 (m, 2H), 7.52 (m, 5H), 5.90 (m, 1H), 5.03 (m, 2H), 3.05 (t, 2H), 2.22 (m, 2H), 2.02 (m, 2H). MS (m/z): 225 [MH]⁺.

Preparation 6: 4-(4-phenyl-2-pyrimidinyl)butanal (P6)

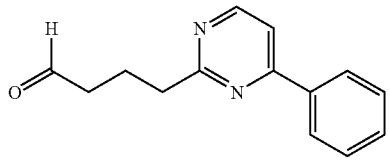

To a stirred solution of 2-(4-penten-1-yl)-4-phenylpyrimidine (P5, 142 mg) in THF/H₂O (5/1 mL) were added OsO₄ (4% in water, 0.2 mL) and NaIO₄ (404 mg). The solution was stirred at room temperature for 0.5 h. Water was then added and the mixture extracted with DCM. The organic phase was washed with brine, dried over Na₂SO₄, filtered and evaporated in vacuo to give 141 mg of the title compound as an oil, which was used in the subsequent step without further purification.

MS (m/z): 227 [MH]⁺.

Preparation 7: 2-(4-penten-1-yl)-4-(trifluoromethyl)pyrimidine (P7)

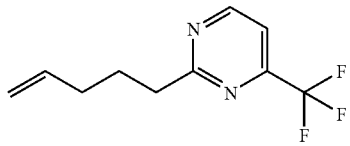

To a solution of 5-hexenimidamide hydrochloride (P4, 200 mg) in ethanol (1.8 mL), sodium ethoxide (92 mg) was added and the mixture stirred at r.t. for 5 min. 4-(Ethyloxy)-1,1,1-trifluoro-3-buten-2-one (0.13 mL) was then added and the mixture was stirred at room temperature for 18 h. The solvent was evaporated, the residue was dissolved in dichloromethane and the organic layer was washed with H₂O and dried over Na₂SO₄. This solution was filtered and the filtrate was concentrated in vacuo. The crude was purified by column chromatography (eluting with dichloromethane/methanol 95/5) to give 143 mg of the title compound.

NMR (¹H, CDCl₃): δ 8.92 (m, 1H), 7.45 (m, 1H), 5.83 (m, 1H), 5.03 (m, 2H), 3.05 (m, 2H), 2.15 (m, 2H), 1.98 (m, 2H). MS (m/z): 217 [MH]⁺.

Preparation 8: 4-[4-(trifluoromethyl)-2-pyrimidinyl]butanal (P8)

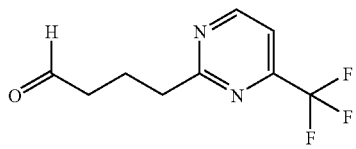

To a solution of 2-(4-penten-1-yl)-4-(trifluoromethyl)pyrimidine (P7, 143 mg) in THF/H₂O 5/1 (6.5 mL) were added OsO₄ (4% in water, 0.2 mL) and NaIO₄ (424 mg). The solution was stirred at r.t. for 30 min. Water was then added and the mixture extracted with DCM. The organic phase was washed with brine, dried over Na₂SO₄, filtered and evaporated in vacuo to give 91 mg of the title compound as an oil, which was used in the subsequent step without further purification.

MS (m/z): 219 [MH]⁺.

Preparation 9: 2-(methylthio)-4-[(phenylmethyl)oxy]pyrimidine (P9)

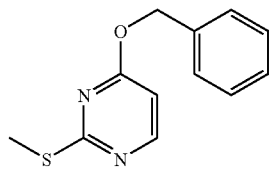

Benzyl alcohol (1.3 mL) was added dropwise to a suspension of sodium hydride (60% in mineral oil, 0.74 g) in 12.4 mL of dry dioxane, and the mixture was stirred at 100° C. for 30 min. A solution of 4-chloro-2-(methylthio)pyrimidine (2.0 g) in dry dioxane (8.2 mL) was added dropwise at 50° C. and the mixture was stirred at this temperature for 5 hours. After cooling at room temperature the mixture was acidified with glacial acetic acid, treated with water and extracted with dichloromethane. The organic phases were dried over anhydrous Na₂SO₄ filtered and concentrated under reduced pressure. The crude product was purified by a silica SPE cartridge (70 g) eluting with ciclohexane/ethyl acetate from 95/5 to 9/1 to give the title compound as a white solid (1.22 g).

NMR (¹H, CDCl₃): δ 8.25 (d, 1H), 7.50-7.25 (m, 5H), 6.42 (d, 1H), 5.40 (s, 2H), 2.53 (s, 3H). MS (m/z): 233 [MH]⁺.

Preparation 10: 2-(methylsulfonyl)-4-[(phenylmethyl)oxy]pyrimidine (P10)

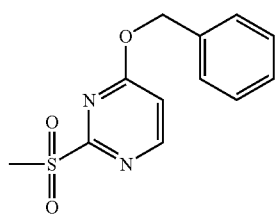

To a solution of 2-(methylthio)-4-[(phenylmethyl)oxy]pyrimidine (P9, 245 mg) in THF/MeOH 1/1 (15.6 mL) was added a solution of Oxone® (2.6 g) in water (14 mL). After 40 min a saturated NaHCO₃ solution was added and the mixture was extracted with ethyl acetate. The organic phase was washed with brine, dried over anhydrous Na₂SO₄ filtered and concentrated under reduced pressure. The crude product was purified by a silica SPE cartridge (10 g) eluting with dichloromethane/methanol from 100/0 to 99/1 to give the title compound as a white solid (230 mg).

NMR ($^1$H, CDCl$_3$): δ 8.55 (d, 1H), 7.50-7.30 (m, 5H), 6.95 (d, 1H), 5.50 (s, 2H), 3.30 (s, 3H).

MS (m/z): 287 [MNa]$^+$.

Preparation 11: 3-{(1S,5R)-1-[4-(trifluoromethyl)phenyl]-3-azabicyclo[3.1.0]hex-3-yl}-1-propanol (P11)

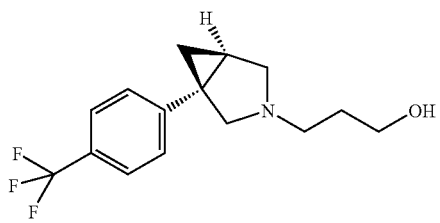

To a solution of (1S,5R)-1-[4-(trifluoromethyl)phenyl]-3-azabicyclo[3.1.0]hexane (151 mg, prepared following the procedure reported in WO 2005080382) in dry tetrahydrofuran (3.3 mL), triethylamine (0.112 mL), 3-bromo-1-propanol (0.073 mL) and NaI were added and the resulting mixture was heated at reflux for 4 hours. After cooling at room temperature it was diluted with ethyl acetate (20 mL), washed with water, dried over anhydrous Na$_2$SO$_4$ and concentrated under reduced pressure. The crude product was purified by a silica SPE cartridge (10 g) eluting with dichloromethane/methanol from 99/1 to 97/3 to give the title compound as a colourless oil (144 mg).

NMR ($^1$H, CDCl$_3$): δ 7.50 (d, 2H), 7.19 (d, 2H), 4.85 (bs, 1H), 3.85 (t, 2H), 3.58 (d, 1H), 3.33 (d, 1H), 2.80 (m, 2H), 2.62 (dd, 1H), 2.50 (dd, 1H), 1.82 (m, 2H), 1.72 (m, 1H), 1.38 (t, 1H), 0.91 (dd, 1H).

MS (m/z): 286 [MH]$^+$.

Preparation 12: (1S,5R)-3-[3-({4-[(phenylmethyl)oxy]-2-pyrimidinyl}oxy)propyl]-1-[4-(trifluoromethyl)phenyl]-3-azabicyclo[3.1.0]hexane (P12)

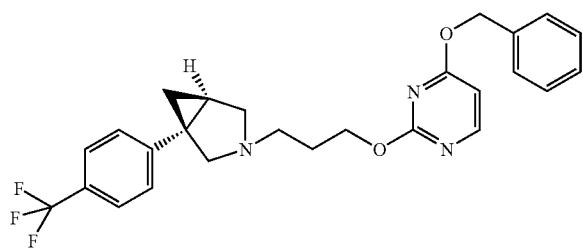

To a solution of 3-{(1S,5R)-1-[4-(trifluoromethyl)phenyl]-3-azabicyclo[3.1.0]hex-3-yl}-1-propanol (P11, 144 mg) in dry DMF (1.8 mL) NaH (60% in mineral oil, 24 mg) was added at 0° C. The mixture was stirred at this temperature for 10 min, then at room temperature for 15 min. A solution of 2-(methylsulfonyl)-4-[(phenylmethyl)oxy]pyrimidine (135 mg) in dry DMF (1.1 mL) was then added. The reaction mixture was stirred at room temperature for 5 hours, then hydrolysed with water and extracted with ethyl acetate. The organic phase was washed with brine, dried over anhydrous Na$_2$SO$_4$ and concentrated under reduced pressure. The crude product was purified by a silica SPE cartridge (5 g) eluting with dichloromethane/methanol from 100/0 to 98/2 to give the title compound as a colourless oil (171 mg).

NMR ($^1$H, CDCl$_3$): δ 8.21 (d, 1H), 7.54 (d, 2H), 7.48-7.30 (m, 5H), 7.22 (d, 2H), 6.42 (d, 1H), 5.42 (s, 2H), 4.45 (t, 2H), 3.42 (d, 1H), 3.18 (d, 1H), 2.78-2.40 (m, 4H), 2.03 (m, 2H), 1.78 (m, 1H), 1.53 (m, 1H), 0.83 (m, 1H).

MS (m/z): 470 [MH]$^+$.

Preparation 13: (1S,5R)-1-[2-fluoro-4-(trifluoromethyl)phenyl]-3-azabicyclo[3.1.0]hexane (P13)

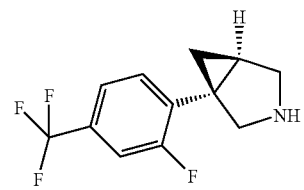

The title compound was prepared as reported in WO2005080382.

Preparation 14: (1S,5R)-3-(3-Chloropropyl)-1-[2-fluoro-4-(trifluoromethyl)phenyl]-3-azabicyclo[3.1.0]hexane (P14)

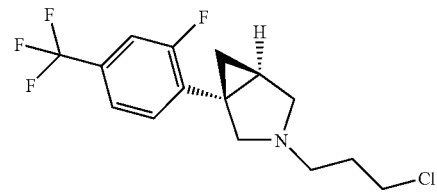

To a solution of (1S,5R)-1-[2-fluoro-4-(trifluoromethyl)phenyl]-3-azabicyclo[3.1.0]hexane (P13, 426 mg) in dry tetrahydrofuran (9 mL), triethylamine (0.79 mL) and 1-bromo-3-chloropropane (0.37 mL) were added and the resulting mixture was refluxed for 16 hours. After cooling at room temperature it was concentrated in vacuo, diluted with ethyl acetate, washed with a saturated solution of NaHCO$_3$ in water and brine, dried over anhydrous Na$_2$SO$_4$ and concentrated under reduced pressure. The crude product was purified by chromatography (silica gel) eluting with cyclohexane/EtOAc 8:2 to give the title compound as yellow oil (582 mg).

NMR ($^1$H, CDCl$_3$): δ 7.24 (d, 2H), 7.16 (t, 1H), 3.51 (t, 2H), 3.18 (dd, 1H), 3.03 (d, 1H), 2.54 (t, 2H), 2.48 (dd, 1H), 2.37 (d, 1H), 1.83 (m, 2H), 1.69 (m, 1H), 1.34 (t, 1H), 0.70 (dd, 1H).

MS (m/z): 322 [MH]$^+$.

Preparation 15: 2-(4-penten-1-yl)-4-pyrimidinol (P15)

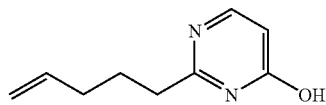

The title compound was prepared in 56 mg yield as a colorless oil from 5-hexenimidamide hydrochloride (P4, 200 mg) and ethyl-3-(ethyloxy)-2-propenoate (130 mg) in analogy to the method described in Preparation 7, but heating the reaction mixture at 80° C. MS (m/z): 165 [MH]+.

Preparation 16: 4-(4-hydroxy-2-pyrimidinyl)butanal (P16)

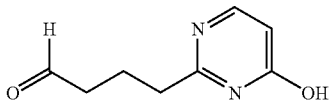

The title compound was prepared in 58 mg yield as a brown oil from 2-(4-penten-1-yl)-4-pyrimidinol (P15, 57 mg) in analogy to the method described in Preparation 6.

MS (m/z): 167 [MH]+.

Preparation 17 and 18: (1R,5R or 1S,5S)-1-[5-(trifluoromethyl)-2-pyridinyl]-3-azabicyclo[3.1.0]texane (P17, Enantiomer 1) and (1S,5S or 1R,5R)-1-[5-(trifluoromethyl)-2-pyridinyl]-3-azabicyclo[3.1.0]texane (P18, Enantiomer 2)

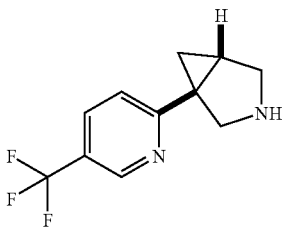

1-[5-(trifluoromethyl)-2-pyridinyl]-3-azabicyclo[3.1.0]texane was prepared as reported in WO2005080382. A chiral separation of this racemic mixture (166 mg) was performed to afford the separated enantiomers by preparative chromatography using a chiral column Chiralcel OD (25×0.46 cm), eluent A: n-hexane; B: ethanol+0.1% isopropylamine, gradient isocratic 5% B, flow rate 1 mL/min, detection UV at 225 nm.

Preparation 17: title compound (P17, Enantiomer 1) was recovered in 23 mg yield as a colorless oil (166 mg), retention time=11.2 min.

Preparation 18: title compound (P18, Enantiomer 2) was recovered in 16 mg yield as a colorless oil (166 mg), retention time=16.3 min.

MS (m/z): 229 [MH]+.

Preparation 19: (1S,5S or 1R,5R)-3-(3-chloropropyl)-1-[5-(trifluoromethyl)-2-pyridinyl]-3-azabicyclo[3.1.0]hexane (Enantiomer 2) (P19)

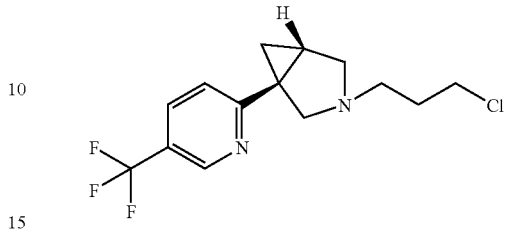

The title compound was prepared in 10 mg yield as a colorless oil from (1S,5S or 1R,5R)-1-[5-(trifluoromethyl)-2-pyridinyl]-3-azabicyclo[3.1.0]texane (P18, 16 mg) in analogy to the method described in Preparation 14.

MS (m/z): 305 [MH]+.

Preparation 20: (1R,5S/1S,5R)-1-[4-(1-methylethyl)phenyl]-3-azabicyclo[3.1.0]hexane-2,4-dione (P20)

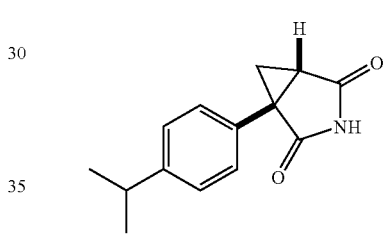

To a slurry of maleimide (1.4 g), anhydrous CuCl$_2$ (1.2 g) and tert-butyl nitrite (1.3 mL) in CH$_3$CN (11 mL) at room temperature a solution of 4-(1-methylethyl)aniline (1.0 g) in CH$_3$CN (7 mL) was added dropwise. The reaction mixture was stirred at room temperature for 18 h and 6N aqueous HCl was added. The mixture was extracted with diethyl ether, the organic layer was washed with saturated aqueous NaCl and dried over Na$_2$SO$_4$. The solution was filtered and the filtrate was concentrated in vacuo. By NMR analysis the crude mixture resulted a 1:1.6 mixture of the arylated maleimide hydrogen chloride adduct and unreacted maleimide.

A DMSO (33 mL) solution of this crude product was added dropwise to a preformed solution of trimethylsulfoxonium iodide (4.8 g) in anhydrous DMSO (66 mL) to which NaH (60% dispersion in mineral oil, 1.3 g) had been added portionwise. The reaction mixture was stirred for 4 hours and a saturated aqueous NH$_4$Cl solution was added. The reaction mixture was extracted with Et$_2$O and the combined organic layers were washed with water and saturated aqueous NaCl and dried over Na$_2$SO$_4$. The solution was filtered and the filtrate was concentrated in vacuo to give the title compound as an orange solid (1.5 g), which was used without further purification.

MS (m/z): 230 [MH]+.

Preparation 21: (1R,5S/1S,5R)-1-[4-(1-methylethyl)phenyl]-3-azabicyclo[3.1.0]hexane (P21)

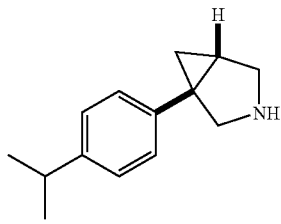

To a solution of 1-[4-(1-methylethyl)phenyl]-3-azabicyclo[3.1.0]hexane-2,4-dione (P20, 1.5 g) in anhydrous tetrahydrofuran (45 mL), BH₃ in tetrahydrofuran (1 M, 26 mL) was added at 0° C. The reaction mixture was stirred at 65° C. for 6 hours, then cooled to 0° C., 6N aqueous HCl was added and the mixture was refluxed for 3 hours. The mixture was then basified with 5N aqueous NaOH and extracted with diethyl ether, the organic layer was washed with saturated aqueous NaCl and dried over Na₂SO₄. The solution was filtered and the filtrate was concentrated in vacuo. The crude compound was purified by a SCX cartridge (strong cationic exchanger, 10 g) eluting with MeOH (150 mL) and then NH₃ 0.3M in MeOH (100 mL) to give the title compound as colourless oil (0.5 g).

MS (m/z): 202 [MH]⁺.

Preparation 22: (1R,5S/1S,5R)-3-(3-chloropropyl)-1-[4-(1-methylethyl)phenyl]-3-azabicyclo[3.1.0]hexane

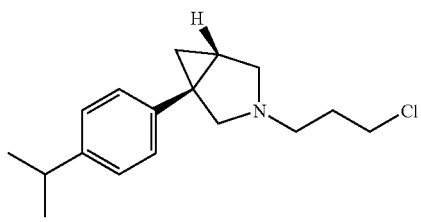

The title compound was prepared in 66 mg yield as a colorless oil from (1R,5S/1S,5R)-1-[4-(1-methylethyl)phenyl]-3-azabicyclo[3.1.0]hexane (P21, 100 mg) in analogy to the method described in Preparation 14.

NMR (¹H, CDCl₃): δ=0.80 (m, 1H), 1.25 (d, 6H), 1.38 (m, 1H), 1.68 (m, 1H), 1.95 (m, 2H), 2.48 (m, 1H), 2.55-2.68 (m, 3H), 2.90 (sept, 1H), 3.12 (d, 1H), 3.33 (d, 1H), 3.63 (t, 2H), 7.09 (d, 2H), 7.19 (d, 2H). MS (m/z): 278 [MH]⁺.

Example 1

(1S,5R)-3-[4-(4-phenyl-2-pyrimidinyl)butyl]-1-[4-(trifluoromethyl)phenyl]-3-azabicyclo[3.1.0]hexane hydrochloride (E1)

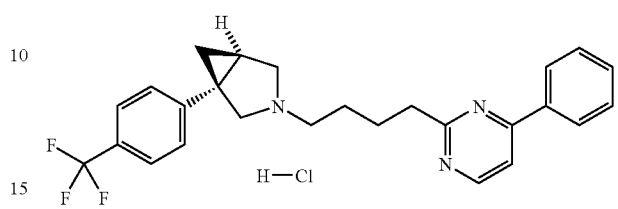

A mixture of (1S,5R)-1-[4-(Trifluoromethyl)phenyl]-3-azabicyclo[3.1.0]hexane (P1, 55 mg), 4-(4-phenyl-2-pyrimidinyl)butanal (P6, 55 mg), NaBH(OAc)₃ (102 mg) and AcOH (0.02 mL) in THF (anhydrous, 2.4 mL) was stirred at r.t. for 2 h. NaOH 1N was added and the mixture was evaporated in vacuo. The residue was dissolved in dichloromethane and the organic layer was washed with saturated NaHCO₃, brine and dried over Na₂SO₄. This solution was filtered and the filtrate was concentrated in vacuo. The crude was purified by column chromatography (eluting with dichloromethane/methanol 98/2) to give 45 mg of the free base of the title compound. To a solution of this material in DCM (0.5 mL) was added HCl (1M in Et₂O, 0.1 mL), the solvent evaporated in vacuo and the material thus obtained triturated with Et₂O to give 43 mg of the title compound as a white slightly hygroscopic solid.

NMR (¹H, DMSO-D6): δ 10.16 (bs, 1H), 8.78 (d, 1H), 8.21 (m, 2H), 7.91 (d, 1H), 7.69 (d, 2H), 7.57 (m, 3H), 7.47 (d, 2H), 4.02 (m, 1H), 3.70 (m, 1H), 3.61 (t, 1H), 3.49 (m, 1H), 3.24 (m, 2H), 2.98 (t, 2H), 2.27 (m, 1H), 1.89 (m, 2H), 1.79 (m, 2H), 1.60 (m, 1H), 1.18 (m, 1H). MS (m/z): 438 [MH]⁺.

Example 2

(1S,5R1)-[4-(trifluoromethyl)phenyl]-3-{4-[4-(trifluoromethyl)-2-pyrimidinyl]butyl}-3-azabicyclo[3.1.0]hexane hydrochloride (E2)

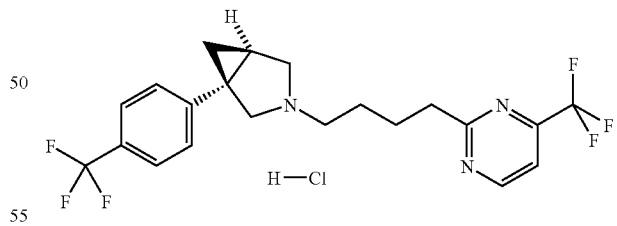

A mixture of (1S,5R)-1-[4-(trifluoromethyl)phenyl]-3-azabicyclo[3.1.0]hexane (P1, 51 mg), 4-[4-(trifluoromethyl)-2-pyrimidinyl]butanal (P8, 49 mg), NaBH(OAc)₃ (93 mg) and AcOH (0.018 mL) in THF (2.2 mL) was stirred at r.t. for 2 h. NaOH 1N was added and the mixture was evaporated in vacuo. The residue was dissolved in dichloromethane and the organic layer was washed with saturated NaHCO₃, brine and dried over Na₂SO₄. This solution was filtered and was concentrated in vacuo. The crude was purified by column chromatography (eluting with dichloromethane/methanol 98/2) to give 46 mg of the free base of the title compound. To a solution of this material in DCM (0.5 mL) was added HCl (1M in Et$_2$O, 0.1 mL), the solvent evaporated in vacuo and the material thus obtained triturated with Et$_2$O to give 46 mg of the title compound as a white slightly hygroscopic solid.

NMR ($^1$H, DMSO-D6): δ 10.31 (bs, 1H), 9.12 (d, 1H), 7.88 (d, 1H), 7.69 (d, 2H), 7.48 (d, 2H), 4.03 (m, 1H), 3.70 (m, 1H), 3.60 (t, 1H), 3.47 (t, 1H), 3.22 (m, 2H), 3.02 (t, 2H), 2.27 (m, 1H), 1.80 (m, 4H), 1.65 (m, 1H), 1.18 (m, 1H). MS (m/z): 430 [MH]$^+$.

Examples 3-4

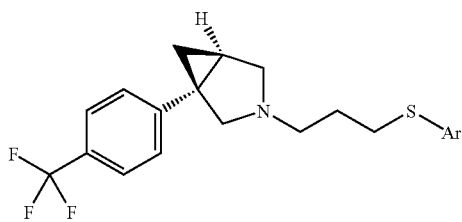

To a solution of the opportune thioaryl (0.082 mmol) in dry acetonitrile (2 ml) 2-tert-butylimino-2-diethylamino-1,3-dimethyl-perhydro-1,3,2-diaza-phosphorine on polystyrene (56 mg, 2.2 mmol/g) was added and the resulting mixture was shaken for 30 minutes at room temperature then (1S,5R)-3-(3-chloropropyl)-1-[4-(trifluoromethyl)phenyl]-3-azabicyclo[3.1.0]hexane (P2, 25 mg) was added and the resulting mixture was shaken at 50° C. overnight. After cooling the resin was filtered off, washed with methanol (2 ml) and then the solvent was removed under reduced pressure. Purifications were carried out using mass directed HPLC using a Waters XTerra Prep MS C18 10 μm, 100×19 mm column using the following conditions:

Mobile phase: A: NH4HCO3 sol. 10 mM, pH10; B: CH3CN

Gradient 1: 30% (B) for 1 min, from 30% (B) to 95% (B) in 9 min, 95% (B) for 3 min Flow rate: 17 ml/min; UV wavelength range: 210-350 nm Mass range: 100-900 amu, Ionization: ES+

Then solvent was removed under reduced pressure to give title compounds as free bases.

HPLC: Analytical

Column: X Terra MS C18 5 μm, 50×4.6 mm

Mobile phase: A: NH4HCO3 sol. 10 mM, pH10; B: CH3CN

Gradient: 30% (B) for 1 min, from 30% (B) to 95% (B) in 9 min, 95% (B) for 3 min Flow rate: 1 ml/min; UV wavelength range: 210-350 nm; Mass range: 100-900 amu, (ES+).

| Example | Name and Structure | R (min) | Analytical data |
|---|---|---|---|
| 3 | (1S,5R)-3-[3-(2-pyrimidinylthio)propyl]-1-[4-(trifluoromethyl)phenyl]-3-azabicyclo[3.1.0]hexane | 8.76 | MS (m/z): 380 [MH]$^+$. |
| 4 | (1S,5R)-3-[3-({4-[4-(methyloxy)phenyl]-2-pyrimidinyl}thio)propyl]-1-[4-(trifluoromethyl)phenyl]-3-azabicyclo[3.1.0]hexane | 5.66 | NMR ($^1$H, DMSO-D6): δ = 8.58 (d, 1H), 8.15 (d, 2H), 7.68 (d, 1H), 7.59 (d, 2H), 7.30 (d, 2H), 7.06 (d, 2H), 3.79 (t, 3H), 3.38 (d, 1H), 3.21 (m, 2H), 3.05 (d, 1H), 2.60 (d, 2H), 2.51 (d, 1H), 2.40 (d, 1H), 1.89 (m, 3H), 1.44 (m, 1H), 0.85 (m, 1H). MS (m/z): 486 [MH]$^+$. |

Example 5

2-[(3-{(1S,5R)-1-[4-(trifluoromethyl)phenyl]-3-azabicyclo[3.1.0]hex-3-yl}propyl)oxy]-4(1H)-pyrimidinone hydrochloride (E5)

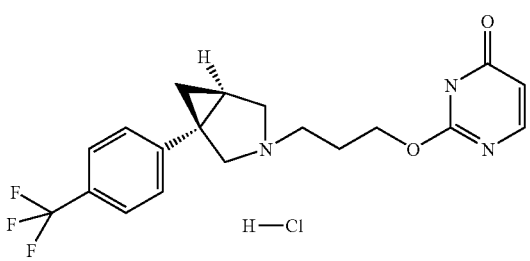

(1S,5R)-3-[3-({4-[(phenylmethyl)oxy]-2-pyrimidinyl}oxy)propyl]-1-[4-(trifluoromethyl)phenyl]-3-azabicyclo[3.1.0]hexane (P12, 121 mg) was dissolved in ethyl acetate (10 mL) and hydrogenated with hydrogen in the presence of 10% Pd/C at atmospheric pressure. After 2 hours the catalyst was filtered off, the filtrate was concentrated and the residue was purified by a silica SPE cartridge (2 g) eluting with dichloromethane/methanol from 99/1 to 95/5 to give 85 mg of the free base of the title compound. To a solution of this material in dichloromethane (1 mL) was added 0.224 mL of HCl (1M in Et$_2$O), the solvent was evaporated in vacuo and the material thus obtained triturated with Et$_2$O to give 93 mg of the title compound as a white slightly hygroscopic solid.

NMR ($^1$H, CDCl$_3$): (free base of the title compound) δ 7.77 (d, 1H), 7.52 (d, 2H), 7.22 (d, 2H), 6.12 (d, 1H), 4.47 (t, 2H), 3.40 (d, 1H), 3.15 (d, 1H), 2.75-2.42 (m, 4H), 2.06-1.93 (m, 2H), 1.78 (m, 1H), 1.50 (m, 1H), 0.83 (m, 1H), NH not observed. MS (m/z): 380 [MH]$^+$.

Example 6

2-[(3-{(1S,5R)-1-[2-fluoro-4-(trifluoromethyl)phenyl]-3-azabicyclo[3.1.0]hex-3-yl}propyl)thio]-4(1H)-pyrimidinone hydrochloride (E6)

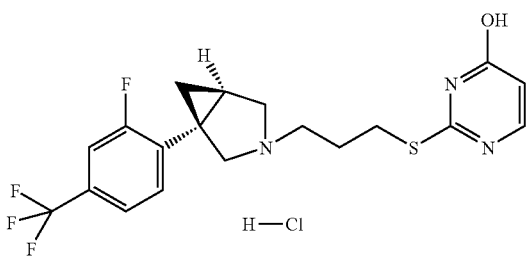

A mixture of (1S,5R)-3-(3-chloropropyl)-1-[2-fluoro-4-(trifluoromethyl)phenyl]-3-azabicyclo[3.1.0]hexane (P14, 70 mg), 2-thioxo-2,3-dihydro-4(1H)-pyrimidinone (33 mg), K$_2$CO$_3$ (36 mg) and NaI (39 mg) in dry dimethylformamide (1.5 mL) was heated at 60° C. for 22 hours. Water was then added and the reaction mixture extracted with ethyl acetate. The organic phase was dried over Na$_2$SO$_4$ and evaporated in vacuo. The crude product was purified by a silica SPE cartridge (2 g) eluting with dichloromethane/methanol from 100/0 to 98/2 to give 38 mg of the free base of the title compound. To a solution of this material in dichloromethane (1 mL) was added 0.092 mL of HCl (1M in Et$_2$O), the solvent was evaporated in vacuo and the material thus obtained triturated with Et$_2$O to give 40 mg of the title compound as a white slightly hygroscopic solid.

NMR ($^1$H, CDCl$_3$) free base of the title compound: δ=0.85 (m, 1H), 1.50 (bs, 1H), 1.80 (m, 1H), 1.85-1.95 (m, 2H), 2.48 (d, 1H), 2.60-2.70 (m, 3H), 3.12-3.3.38 (m, 4H), 6.25 (d, 1H), 7.22-7.40 (m, 3H), 7.85 (d, 1H), OH not observed. MS (m/z): 414 [MH]$^+$.

Example 7

4-[(3-{(1S,5R)-1-[4-(trifluoromethyl)phenyl]-3-azabicyclo[3.1.0]hex-3-yl}propyl)thio]-2(1H)-pyrimidinone hydrochloride (E7)

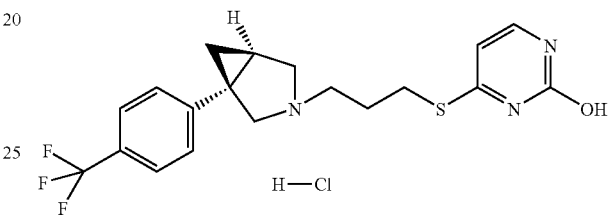

The title compound was prepared in 25 mg yield as a yellow slightly hygroscopic solid from (1S,5R)-3-(3-chloropropyl)-1-[4-(trifluoromethyl)phenyl]-3-azabicyclo[3.1.0]hexane (P2, 70 mg) and 4-thioxo-3,4-dihydro-2(1H)-pyrimidinone (35 mg) in analogy to the method described in Example 6.

NMR ($^1$H, CDCl$_3$) free base of the title compound: δ=12.60 (bs, 1H), 7.53 (d, 2H), 7.40 (d, 1H), 7.25 (d, 2H), 6.28 (d, 1H), 3.52-3.38 (bm, 1H), 3.30 (m, 2H), 3.25-3.10 (bm, 1H), 2.77-2.42 (bm, 4H), 2.05-1.47 (bm, 4H), 1.94-1.82 (bm, 1H). MS (m/z): 396 [MH]$^+$.

Example 8

2-[(3-{(1S,5R)-1-[4-(trifluoromethyl)phenyl]-3-azabicyclo[3.1.0]hex-3-yl}propyl)thio]-4(1H)-pyrimidinone hydrochloride (E8)

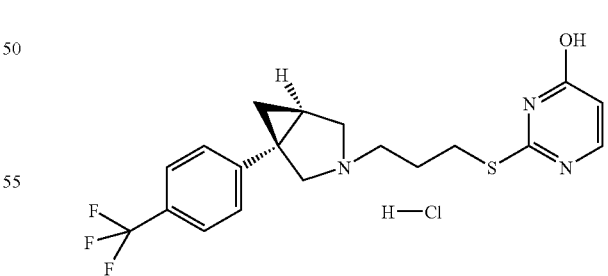

The title compound was prepared in 22 mg yield as a white slightly hygroscopic solid from (1S,5R)-3-(3-chloropropyl)-1-[4-(trifluoromethyl)phenyl]-3-azabicyclo[3.1.0]hexane (P2, 70 mg) and 2-thioxo-2,3-dihydro-4(1H)-pyrimidinone (35 mg) in analogy to the method described in Example 6.

NMR ($^1$H, DMSO-D6): δ=1.08-1.18 (m, 1H), 1.51-1.69 (m, 1H), 1.99-2.14 (m, 2H), 2.17-2.27 (m, 1H), 3.06-3.35 (m,

4H), 3.41-3.52 (m, 1H), 3.50-3.64 (m, 1H), 3.63-3.75 (m, 1H), 3.92-4.10 (m, 1H), 6.05 (bs, 1H), 7.44 (d, 2H), 7.65 (d, 2H), 7.80 (bs, 1H), 10.21 (bs, 1H), 12.75 (bs, 1H).

MS (m/z): 396 [MH]$^+$.

Example 9

(1S,5R)-3-{3-[(4-methyl-2-pyrimidinyl)thio]propyl}-1-[4-(trifluoromethyl)phenyl]-3-azabicyclo[3.1.0]hexane hydrochloride (E9)

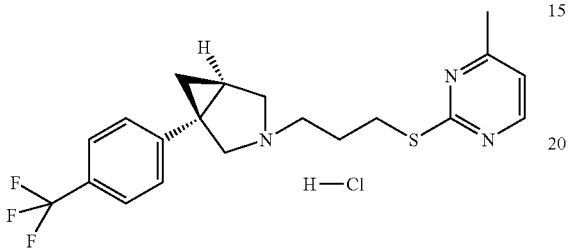

The title compound was prepared in 40 mg yield as a white slightly hygroscopic solid from (1S,5R)-3-(3-chloropropyl)-1-[4-(trifluoromethyl)phenyl]-3-azabicyclo[3.1.0]hexane (P2, 45 mg) and 4-methyl-2(1H)-pyrimidinethione (29 mg) in analogy to the method described in Example 6.

NMR ($^1$H, DMSO-D6): δ=1.17 (t, 1H), 1.71 (t, 1H), 2.07-2.19 (m, 2H), 2.22-2.30 (m, 1H), 2.41 (s, 3H), 3.16 (t, 2H), 3.24-3.32 (m, 2H), 3.43-3.53 (m, 1H), 3.61 (t, 1H), 3.71 (dd, 1H), 4.04 (dd, 1H), 7.11 (d, 1H), 7.47 (d, 2H), 7.69 (d, 2H), 8.48 (d, 1H), 10.51 (bs, 1H). MS (m/z): 394 [MH]$^+$.

Example 10

2-(4-{(1S,5R)-1-[4-(trifluoromethyl)phenyl]-3-azabicyclo[3.1.0]hex-3-yl}butyl)-4(1H)-pyrimidinone hydrochloride (E10)

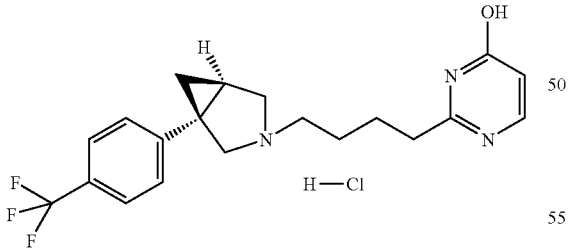

The title compound was prepared in 29 mg yield as a white slightly hygroscopic solid from 4-(4-hydroxy-2-pyrimidinyl)butanal (P16, 58 mg) and (1S,5R)-1-[4-(trifluoromethyl)phenyl]-3-azabicyclo[3.1.0]hexane (P1, 80 mg) in analogy to the method described in Example 1.

NMR ($^1$H, DMSO-D6): δ=1.13-1.20 (m, 1H), 1.61-1.78 (m, 5H), 2.24-2.31 (m, 1H), 2.54-2.61 (m, 2H), 3.14-3.25 (m, 2H), 3.42-3.52 (m, 1H), 3.56-3.63 (m, 1H), 3.64-3.74 (m, 1H), 3.97-4.08 (m, 1H), 6.19 (d, 1H), 7.48 (d, 2H), 7.69 (d, 2H), 7.85 (d, 1H), 10.42 (bs, 1H), 12.46 (bs, 1H). MS (m/z): 378 [MH]$^+$.

Example 11

2-[(3-{(1S,5S or 1R,5R)-1-[5-(trifluoromethyl)-2-pyridinyl]-3-azabicyclo[3.1.0]hex-3-yl}propyl)thio]-4(1H)-pyrimidinone (E11, Enantiomer 2)

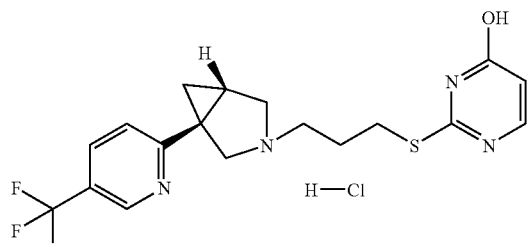

The title compound was prepared in 7 mg yield as a white slightly hygroscopic solid from 3-(3-chloropropyl)-1-[5-(trifluoromethyl)-2-pyridinyl]-3-azabicyclo[3.1.0]hexane (P19, 10 mg) and 2-thioxo-2,3-dihydro-4(1H)-pyrimidinone (5 mg) in analogy to the method described in Example 6.

NMR ($^1$H, CDCl$_3$), free base of the title compound: δ=1.18-1.36 (m, 2H), 1.70 (s, 1H), 1.87-2.12 (m, 3H), 2.52 (m, 1H), 2.70 (m, 2H), 2.88 (m, 1H), 3.13-3.30 (m, 3H), 3.48 (d, 1H), 6.22 (d, 1H), 7.15 (d, 1H), 7.77-7.90 (m, 2H), 8.72 (s, 1H). MS (m/z): 397 [MH]$^+$.

Example 12

2-[(3-{(1R,5S/1S,5R))-1-[4-(1-methylethyl)phenyl]-3-azabicyclo[3.1.0]hex-3-yl}propyl)thio]-4(1H)-pyrimidinone hydrochloride (E12)

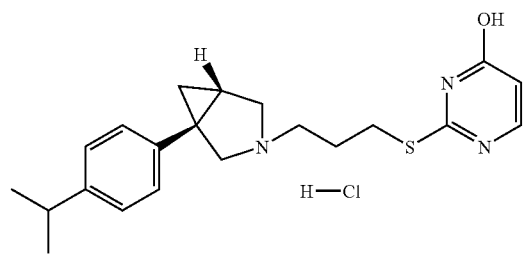

The title compound was prepared in 41 mg yield as a white slightly hygroscopic solid from (1R,5S/1S,5R)-3-(3-chloropropyl)-1-[4-(1-methylethyl)phenyl]-3-azabicyclo[3.1.0]hexane (P21, 66 mg) and 2-thioxo-2,3-dihydro-4(1H)-pyrimidinone (35 mg) in analogy to the method described in Example 6.

NMR ($^1$H, CDCl$_3$), free base of the title compound: δ=0.82 (m, 1H), 1.25 (d, 6H), 1.42 (m, 1H), 1.70 (m, 1H), 1.93 (m, 2H), 2.50 (m, 1H), 2.57-2.70 (m, 3H), 2.90 (sept, 1H), 3.10-3.30 (m, 3H), 3.40 (d, 2H), 6.22 (d, 1H), 7.10 (d, 2H), 7.19 (d, 2H), 7.87 (d, 1H). MS (m/z): 370 [MH]$^+$.

All publications, including but not limited to patents and patent applications, cited in this specification are herein incorporated by reference as if each individual publication were specifically and individually indicated to be incorporated by reference herein as though fully set forth.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims:

The invention claimed is:

1. A compound of formula (I) or a salt thereof:

(I)

wherein:
p in the group $(R_1)_p$ is 0, 1, 2, 3, 4 or 5;
$R_1$ is independently selected from the group consisting of halogen, hydroxy, cyano, $C_{1-4}$alkyl, halo$C_{1-4}$alkyl, $C_{1-4}$alkoxy, halo$C_{1-4}$alkoxy, $C_{1-4}$alkanoyl and $SF_5$;
n is 2 to 4;
$R_2$ is hydrogen or $C_{1-4}$alkyl;
X is —$CH_2$—, —O— or —S—;
Z may be —CH— or N;
A is a group P or P1,
wherein P is;

and P1 is and
Y is hydrogen, —OH, $C_{1-4}$alkyl, halo$C_{1-4}$alkyl, phenyl or a heteroaromatic group, wherein the phenyl and the heteroaromatic group are optionally substituted by one or two substituents selected from the group consisting of $C_{1-4}$alkyl, halo$C_{1-4}$alkyl, hydroxyl, $C_{1-4}$alkoxy and halo$C_{1-4}$alkoxy.

2. A compound as claimed in claim 1, wherein p in the group $(R_1)_p$ is 1.

3. A compound as claimed in claim 1, wherein $R_1$ is $CF_3$.

4. A compound as claimed in claim 1, wherein n is 3 and X is —$CH_2$—, or n is 3 and X is —S—, or n is 3 and X is —O—.

5. A compound as claimed in claim 1, wherein Y is hydrogen, halo$C_{1-4}$alkyl, phenyl wherein the phenyl is optionally substituted by halo$C_{1-4}$alkoxy, —OH or $C_{1-4}$alkyl.

6. A compound as claimed in claim 1, wherein A is the group P.

7. A compound as claimed in claim 1 which is a compound of formula (IL) or a salt thereof:

(IL)

(IL)
wherein p, $R_1$, $R_2$, n, X, A and Z are defined as above for compounds of formula (I).

8. A compound as claimed in claim 1 which is a compound of formula (IN) or a salt thereof:

(IN)

wherein X and Y are as defined for formula (I).

9. A compound as claimed in claim 1 which is
(1S,5R)-3-[4-(4-phenyl-2-pyrimidinyl)butyl]-1-[4-(trifluoromethyl)phenyl]-3-azabicyclo[3.1.0]hexane;
(1S,5R1)-[4-(trifluoromethyl)phenyl]-3-{4-[4-(trifluoromethyl)-2-pyrimidinyl]butyl}-3-azabicyclo[3.1.0]hexane;
(1S,5R)-3-[3-(2-pyrimidinylthio)propyl]-1-[4-(trifluoromethyl)phenyl]-3-azabicyclo[3.1.0]hexane;
(1S,5R)-3-[3-({4-[4-(methyloxy)phenyl]-2-pyrimidinyl}thio)propyl]-1-[4-(trifluoromethyl)phenyl]-3-azabicyclo[3.1.0]hexane;
2-[(3-{(1S,5R)-1-[4-(trifluoromethyl)phenyl]-3-azabicyclo[3.1.0]hex-3-yl}propyl)oxy]-4(1H)-pyrimidinone;
2-[(3-{(1S,5R)-1-[2-fluoro-4-(trifluoromethyl)phenyl]-3-azabicyclo[3.1.0]hex-3-yl}propyl)thio]-4(1H)-pyrimidinone;
4-[(3-{(1S,5R)-1-[4-(trifluoromethyl)phenyl]-3-azabicyclo[3.1.0]hex-3-yl}propyl)thio]-2(1H)-pyrimidinone;
(1S,5R)-3-{3-[(4-methyl-2-pyrimidinyl)thio]propyl}-1-[4-(trifluoromethyl)phenyl]-3-azabicyclo[3.1.0]hexane;
(1S,5R)-3-{3-[(4-methyl-2-pyrimidinyl)thio]propyl}-1-[4-(trifluoromethyl)phenyl]-3-azabicyclo[3.1.0]hexane;
2-(4-{(1S,5R)-1-[4-(trifluoromethyl)phenyl]-3-azabicyclo[3.1.0]hex-3-yl}butyl)-4-pyrimidinol
2-[(3-{(1R,5R)-1-[5-(trifluoromethyl)-2-pyridinyl]-3-azabicyclo[3.1.0]hex-3-yl}propyl)thio]-4-pyrimidinol;
2-[(3-{(1S,5R)-1-[4-(1-methylethyl)phenyl]-3-azabicyclo[3.1.0]hex-3-yl}propyl)thio]-4-pyrimidinol;
or a salt thereof.

10. A process for preparing a compound of formula (I) or a salt thereof as defined in claim 1, the process comprising:

(a) for compounds of formula (I) wherein X is —CH$_2$— and R$_2$ is hydrogen, reacting a compound of formula (II):

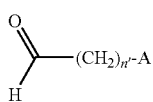
(II)

wherein n and A are as defined for formula (I), with a compound of formula (III):

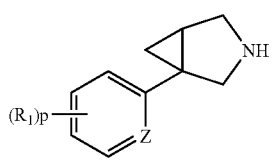
(III)

wherein p, Z and R$_1$ are as defined for formula (I); or (b) for a compound of formula (I), wherein X is —S—, reacting a compound of formula (IV):

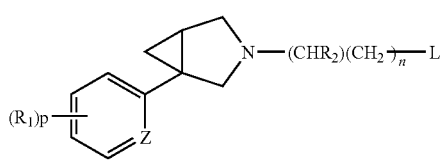
(IV)

wherein p, R$_1$, R$_2$, Z and n are as defined for formula (I) and L is a leaving group, with a compound of formula (V):

HS-A  (V)

wherein A is as defined for formula (I);

(b) for a compound of formula (I), wherein X is —O—, reacting a compound of formula (VI):

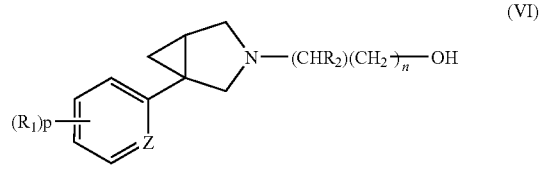
(VI)

wherein p, R$_1$, R$_2$, Z and n are as defined for formula (I), with a compound of formula (VII):

(VII)

wherein A is as defined for formula (I);

and thereafter optionally for process (a), (b) and for process (c):

(i) removing any protecting group(s); and/or (ii) forming a salt; and/or (iii) converting a compound of formula (I) or a salt thereof to another compound of formula (I) or a salt thereof.

11. A pharmaceutical composition comprising a compound as claimed in claim 1 and a pharmaceutically acceptable carrier.

* * * * *